(12) United States Patent
Kleanthous et al.

(10) Patent No.: US 7,569,383 B2
(45) Date of Patent: Aug. 4, 2009

(54) CHIMERIC FLAVIVIRUS VECTORS

(75) Inventors: Harold Kleanthous, Westford, MA (US); Charles Miller, Medford, MA (US); Larisa Oros, Boston, MA (US)

(73) Assignee: Acambis Inc., Cambridge, MA (US)

( * ) Notice: Subject to any disclaimer, the term of this patent is extended or adjusted under 35 U.S.C. 154(b) by 476 days.

(21) Appl. No.: 10/160,939

(22) Filed: May 31, 2002

(65) Prior Publication Data

US 2003/0044773 A1  Mar. 6, 2003

Related U.S. Application Data

(60) Provisional application No. 60/295,265, filed on Jun. 1, 2001.

(51) Int. Cl.
C12N 15/00 (2006.01)
(52) U.S. Cl. .............. 435/320.1; 435/235.1; 424/184.1; 424/199.1; 424/201.1; 424/202.1; 424/204.1; 424/277.1
(58) Field of Classification Search .............. 424/184.1, 424/199.1, 201.1, 202.1, 204.1, 277.1; 435/235.1, 435/320.1
See application file for complete search history.

(56) References Cited

U.S. PATENT DOCUMENTS

| | | | |
|---|---|---|---|
| 6,136,561 | A | 10/2000 | Ivy et al. |
| 6,171,854 | B1 | 1/2001 | Galler et al. |
| 6,184,024 | B1 | 2/2001 | Lai et al. |
| 6,416,763 | B1 | 7/2002 | McDonell et al. |
| 6,682,883 | B1 | 1/2004 | Monath et al. |
| 6,878,372 | B2 | 4/2005 | Monath et al. |
| 2003/0194801 | A1* | 10/2003 | Bonaldo et al. .......... 435/320.1 |
| 2004/0223979 | A1 | 11/2004 | Chambers et al. |
| 2004/0259224 | A1 | 12/2004 | Guirakhoo |
| 2005/0002968 | A1 | 1/2005 | Monath et al. |
| 2005/0053624 | A1 | 3/2005 | Arroyo et al. |
| 2007/0184469 | A1 | 8/2007 | Depres et al. |

FOREIGN PATENT DOCUMENTS

| | | |
|---|---|---|
| WO | WO 93/06214 | 4/1993 |
| WO | WO 98/37911 | 9/1998 |
| WO | WO 01/39802 A1 | 6/2001 |
| WO | WO 02/072835 A1 | 9/2002 |
| WO | WO 02/102828 | 12/2002 |
| WO | WO 03/063725 | 8/2003 |
| WO | WO 03/101397 | 12/2003 |
| WO | WO 03/103571 | 12/2003 |
| WO | WO 2004/045529 | 6/2004 |
| WO | WO 2005/040390 | 5/2005 |
| WO | WO 2005/049815 | 6/2005 |
| WO | WO 2005/082020 | 9/2005 |
| WO | WO 2006/044857 | 4/2006 |
| WO | WO 2006/116182 | 11/2006 |
| WO | WO 2007/051267 | 5/2007 |

OTHER PUBLICATIONS

Chambers, T, et al, 1999 Journal of Virology vol. 73 (4), 3095-3101.*
Dermine et al. (Biochem Biophys Acta 2004 Vol 1704, pp. 11-35).*
Arroyo et al., "Molecular Basis for Attenuation of Neurovinlence of a Yellow Fever Virus/Japanese Encephalitis Virus Chimera Vaccine (ChimeriVax-JE)," J. Virology 75(2):934-942, 2001.
Bonaldo et al., "Surface Expression of an Immunodominant Malaria Protein B Cell Epitope by Yellow Fever Virus," J. Mol. Biol 315:873-885, 2002.
Bonaldo et al., "The Yellow Fever 17D Vaccine Virus as a Vector for the Expression of Foreign Proteins: Development of the New Live Flavivirus Vaccines," Mem Inst Oswaldo Cruz, Rio de Janeiro 95(Suppl. 1):215-223, 2000.
De Vries et al., "Genetic Manipulation of Equine Arteritis Virus Using Full-Length cDNA Clones: Separation of Overlapping Genes and Expression of a Foreign Epitope," Virology 270:84-97, 2000.
Li et al., "Chimeric Influenza Virus Induces Neutralizing Antibodies and Cytotoxic T Cells against Human Immunodeficiency Virus Type 1," J. Virology 67(11):6659-6666, 1993.
McAllister et al., "Recombinant Yellow Fever Viruses are Effective Therapeutic Vaccines for Treatment of Murine Experimental Solid Tumors and Pulmonary Metastases," J. Virology 74(19):9197-9205, 2000.
Rey et al., "The Envelope Glycoprotein from Tick-Borne Encephalitis Virus at 2 Å Resolution," Nature 375:291-298, 1995.
Hurrelbrink et al., "Attenuation of Murray Valley Encephalitis Virus by Site-Directed Mutagenesis of the HInge and Putative Receptor-Binding Regions of the Envelope Protein," Journal of Virology, 75:7692-7702, 2001.
Thomas J. Chambers et al., U.S. Appl. No. 09/121,587, "Chimeric Flavivirus Vaccines," Filed: Jul. 23, 1998.
Thomas J. Chambers et al., U.S. Appl. No. 09/452,638, "Chimeric Flavivirus Vaccines," Filed: Dec. 1, 1999.
Chambers et al., "Yellow Fever/Japanese Encephalitis Chimeric Viruses: Construction and Biological Properties," Journal of Virology 73:3095-3101 (1999).
Goryshin et al., "In5 In Vitro Transposition," J. Biol. Chem. 273:7387-7374 (1998).
Guirakhoo et al., "Construction, Safety, and Immunogenicity in Nonhuman Primates of a Chimeric Yellow Fever-Dengue Virus Tetravalent Vaccine," Journal of Virology 75(16):7290-7304 (2001).
Guirakhoo et al., "Recombinant Chimeric Yellow Fever-Dengue Type 2 Virus is Immunogenic and Protective in Nonhuman Primates," Journal of Virology 74(12):5477-5485 (2000).
Kolaskar et al, "Prediction of Three-Dimensional Structure and Mapping of Conformational Epitopes of Envelope Glycoprotein of Japanese Encephalitis Virus," Virology 261:31-42 (1999).

(Continued)

*Primary Examiner*—Bruce Campell
*Assistant Examiner*—Myron G Hill
(74) *Attorney, Agent, or Firm*—Clark & Elbing LLP

(57) ABSTRACT

The invention provides chimeric flavivirus vectors including foreign peptides inserted into the envelope proteins of the vectors and methods of using these vectors.

**37 Cla

OTHER PUBLICATIONS

Monath et al., "Chimeric Yellow Fever Virus 170-Japanese Encephalitis Virus Vaccine: Dose-Response Effectiveness and Extended Safety Testing in *Rhesus* Monkeys," Journal of Virology 74(4):1742-1751 (2000).

U.S. Appl. No. 08/807,445, filed Feb. 28, 1997, Chambers et al.

U.S. Appl. No. 09/007,664, filed Jan. 15, 1998, Chambers et al.

Allison et al., "Mapping of Functional Elements in the Stem-Anchor Region of Tick-Borne Encephalitis Virus Envelope Protein E," *J. Virology* 73:5605-5612, 1999.

Allison et al., "Mutational Evidence for an Internal Fusion Peptide in Flavivirus Envelope Protein E," *J. Virology* 75:4268-4275, 2001.

Arroyo et al., "Yellow Fever Vector Live-Virus Vaccines: West Nile Virus Vaccine Development," *Trends Mol. Med.* 7:350-354, 2001.

Arroyo et al., "ChimeriVax-West Nile Virus Live-Attenuated Vaccine: Preclinical Evaluation of Safety, Immunogenicity, and Efficacy," *J. Virology* 78:12497-12507, 2004.

Bancroff, "Current Status of Dengue Vaccines and Prospects for the Future," *Puerto Rico Health Sci. J.* 6(1):23-26, 1987. Abstract only.

Barrett, "Current Status of Flavivirus Vaccines," *Ann. N. Y. Acad. Sci.* 951:262-271, 2001.

Bonaldo et al., "Attenuation of Recombiinant Yellow Fever 17-D Viruses Expressing Foreign Protein Epitopes at the Surface," *J. Virology* 79:8602-8613, 2005.

Bonaldo et al., "Expression of Foreign Protein Epitopes at the Surface or Recombinant Yellow Fever 17D Viruses Based on Three-Dimensional Modeling of Its Envelope Protein," *Cell Biochem. Biophys.* 44:313-324, 2006.

Bray et al., "Construction of Intertypic Chimeric Dengue Viruses by Substitution of Structural Protein Genes," *Proc. Natl. Acad. Sci. U.S.A.* 88:10342-10346, 1991.

Bray et al., "Genetic Determinants Responsible for Acquisition of Dengue Type 2 Virus Mouse Neurovirulence," *J. Virology* 72:1647-1651, 1998.

Cardosa, "Dengue Vaccine Design: Issues and Challenges," *British Med. Bull.* 54(2):395-405, 1998.

Carle et al., "Experiments on the Transmission of an Icterogenic Agent in Yellow Fever Vaccine to Horses and Swine," *J. Bacteriol.* 48:45-69, 1944.

Caufour et al., "Constuction, Characterization and Immunogenicity of Recombinant Yellow Fever 17D-Dengue Type 2 Viruses," *Virus Res.* 79:1-14, 2001.

Chambers et al., "Mutagenesis of the Yellow Fever Virus NS2B/3 Cleavage Site: Determinants of Cleavage Site Specificity and Effects on Polyprotein Processing and Viral Replication," *J. Virology* 69(3):1600-1605, 1995.

Chambers et al., "Vaccine Developement Against Dengue and Japanese Encephalitis: Report of a World Health Organization Meeting," *Vaccine* 15:1494-1502, 1997.

Chen et al., "Generation and Characterization of Organ-Tropism Mutants of Japaneses Encephalitis Virus In Vivo and In Vitro," *Virology* 223:79-88, 1996.

Cola et al., "Nucleotide and Complete Amino Acid Sequences of Kunjin Virus: Definitive Gene Order and Characteristics of the Virus-Specified Proteins," *J. Gen. Virol.* 69:1-21, 1988.

Davis et al., "West Nile Virus Recombinant DNA Vaccine Protects Mouse and Horse from Virus Challenge and Expressions in Vitro a Noninfectious Recombinant Antigen That Can Be Used in Enzyme-Linked Immunosorbent Assays," *J. Virology* 75:4040-4047, 2001.

dos Santos et al., "Complete Nucleotide Sequence of Yellow Fever Virus Vaccine Strains 17DD and 17D-213," *Virus Res.* 35:35-41, 1995.

dos Santos et al., "Determinants in the Envelope E Protein and Viral RNA Helicase NS3 that Influence the Induction of Apoptosis in Response to Infection with Dengue Type 1 Virus," *Virology* 274:292-308, 2000.

Edelman et al., "Phase I Trial of 16 Formulations of a Tetravalent Live-Attenuated Dengue Vaccine," *Am. J. Trop. Med. Hyg.* 69(Suppl 6):48-60, 2003.

Galler et al., "The Yellow Fever 17D Vaccine Virus: Molecular Basis of Viral Attenuation and its Use as an Expression Vector," *Braz. J. Biol. Res.* 30:157-168, 1997.

Galler et al., "Genetic Variability Among Yellow Fever Virus 17D Substrains," *Vaccine* 16:1-5, 1998.

Guirakhoo et al., "Immunogenicity, Genetic Stability, and Protective Efficacy of a Recombinant, Chimeric Yellow Fever-Japanese Encephalitis Virus (ChimeriVax-JE) as a Live, Attenuated Vaccine Candidate Against Japanese Encephalitis," *Virology* 257:363-372, 1999.

Guirakhoo et al., "Construction, Viremia, and Immunogenicity Profile of Recombinant Chimeric Yellow Fever/Dengue Viruses in Non-human Primates," Program and Abstracts of the 49th Annual Meeting of the American Society of Tropical Medicine and Hygiene, Houston, Texas, Oct. 29-Nov. 2, 2000, Supplement to *Am. J. Trop. Med. Hyg.*, 313, Abstract.

Guirakhoo et al., "Construction, Viremia, and Immunogenicity Profile of Recombinant Chimeric Yellow Fever/Dengue Viruses in Non-human Primates," Program and Abstracts of the 49th Annual Meeting of the American Society of Tropical Medicine and Hygiene, Houston, Texas, Oct. 29-Nov. 2, 2000, Supplement to *Am. Trop. Med. Hyg.*, 1722, Abstract.

Guirakhoo et al., "Development of ChimeriVax™—Yellow Fever Based Vaccines for Dengue and Japanese Encephalitis Viruses," 6th International Symposium on Positive Strand RNA Viruses, Paris, May 28-Jun. 2, 2001, Abstract.

Guirakhoo et al., "Viremia and Immunogenicity in Nonhuman Primates of a Tetravalent Yellow Fever-Dengue Chimeric Vaccine: Genetic Reconstructions, Dose Adjustment, and Antibody Response Against Wild-Type Dengue Virus Isolates," *Virology* 298:146-159, 2002.

Guirakhoo et al., "Safety and Efficacy of Chimeric Yellow Fever-Dengue Virus Tetravalent Vaccine Formulations in Nonhuman Primates," *J. Virology* 78(9):4761-4775, 2004.

Guirakhoo et al., "A Single Amino Acid Substitution in the Envelope Protein of Chimeric Yellow Fever-Dengue 1 Vaccine Virus Reduces Neurovirulence for Suckling Mice and Viremia/Visceroptropism for Monkeys," *J. Virology* 78(18):9998-10008, 2004.

Guirakhoo et al., "Live Attenuated Chimeric Yellow Fever Dengue Type 2 (ChimerIVax™—DEN2) Vaccine: Phase I Clinical Trial for Safety and Immunogenicity," *Human Vaccines* 2(2):60-67, 2006.

Guy et al., "Evaluation by Flow Cytometry of Antibody-Dependent Enhancement (ADE) of Dengue Infection by Sera from Thai Children Immunized with a Live-Attenuated Tetravalent Dengue Vaccine," *Vaccine* 22:3563-3574, 2004.

Halstead and Deen, "Rapid Review: The Future of Dengue Vaccines," *The Lancet* 360:1243-1245, 2002.

Innis and Eckeis, "Progress in Development of a Live-Attenuated, Tetravalent Dengue Virus by the United States Army Medical Research and Material Command," *Am. J. Trop. Med. Hyg.* 69(Suppl 6):1-4, 2003.

Johnson et al., "Growth Characteristics of Chimerivax™—Den2 Vaccine Virus in *Aedes aegypti* and *Aedes albopictus* Mosquitoes," *Am. J. Trop. Med. Hyg.* 67:260-265, 2002.

Kanesa-thasan et al., "Safety and Immunogenicity of Attenuated Dengue Virus Vaccines (Aventis Pasteur) in Human Volunteers," *Vaccine* 19:3179-3188, 2001.

Kurane et al., "Immunity and Immunopathology in Dengue Virus Infections," *Sem. Immunol.* 4(2):121-127, 1992, Abstract only.

Lai et al., "Evaluation of Molecular Strategies to Develop a Live Dengue Vaccine," *Clin. Diag. Virol.* 10:173-179, 1998.

Lai and Monath, "Chimeric Flaviviruses: Novel Vaccines Against Dengue Fever, Tick-Borne Encephalitis, And Japanese Encephalitis," *Adv. Virus Res.* 61:469-509, 2003.

Laoprasopwattana et al., "Dengue Virus (DV) Enhancing Antibody Activity in Preillness Plasma does not Predict Subsequent Disease Severity or Viremia in Secondary DV Infection," *J. Infect. Dis.* 192:510-519, 2005. Erratum in *J. Infect. Dis.* 192:1863, 2005.

Lee et al., "Changes in the Dengue Virus Major Envelope Protein on Passaging and Their Localization on the Three-Dimensional Structure of the Protein," *Virology* 232:281-290, 1997.

Lee and Lobigs, "Mechanism of Virulence Attenuation of Glycosaminoglycan-Binding Variants of Japanese Encephalitis Virus and Murray Valley Encephalitis Virus," *J. Virology*, 76:4901-4911, 2002.

Mandl et al., "Sequence of the Genes Encoding the Structural Proteins of the Low-Virulence Tick-Borne Flavivirues Langat TP21 and Yelantsev," *Virology* 185:891-895, 1991.

Mandl et al., "Complete Genomic Sequence of Powassen Virus: Evaluation of Genetic-Elements in Tick-Borne Versus Mosquito-Borne Flaviviruses," *Viology* 194:173-184, 1993.

Mandl et al., "Attenuation of Tick-Borne Encephalitis Virus by Structure-Based Site-Specific Mutagenesis of a Putative Flavivirus Receptor Binding Site," *J. Virology*, 74:9601-9609, 2000.

Mandl et al., "Adaptation of Tick-Borne Encephalitis Virus to BHK-21 Cells Results in the Formation of Multiple Heparan Sulfite Binding Sites in the Envelope Protein and Attenuation In Vivo,"*J. Virology* 75:5627-5637, 2001.

Marchevsky et al., "Phenotypic Analysis of Yellow Fever Virus Derived from Complementary DNA," *Am. J. Trop. Med. Hyg.* 52:75-80, 1995.

McMinn, "The Molecular Basis of Virulence of the Enceophalitogenic Flaviviruses," *J. Gen. Virology* 78:2711-2722, 1997.

Modis et al., "A Ligand-Binding Pocket in the Dengue Virus Envelope Glycoprotein," *Proc. Natl. Acad. Sci. U.S.A.* 100(12):6986-6991, 2003.

Monath et al., "Recombinant, Chimaeric Live, Attenuated Vaccine (ChimerVax™) Incorporating the Envelope Genes of Japanese Encephalitis (SA 14-14-2) Virus and the Capsid and Nonstructural Genes of Yellow Fever (17D) Virus is Safe, Immunogenic and Protective in Non-Human Primates," *Vaccine* 17:1669-1882, 1999.

Monath, "Molecular Distinctions Between Attenuated (Vaccine) and Virulent Yellow Fever Viruses," In, Plolkin SA and Orenstein WA (eds.), Vaccines, $3^{rd}$ edition, Saunders (Philadelphia), pp. 815-879, 1999.

Monath et al., "Yellow Fever 17D as a Vector for Vaccines Against Heterologus Flaviviruses," American Society for Virology, $19^{th}$ Annual Meeting, Colorado State Univerisity, Fort Collins, Colorado, Jul. 8-12, 2000, Abstract W17-7, p. 85.

Monath, "Prospects for Development of a Vaccine Against the West Nile Virus," *Ann. N.Y. Acad. Sci.* 951:1-12, 2001.

Monath et al., "West Nile Virus Vaccine," *Curr. Drug Targets Infect. Disord.* 1:1-14, 2001.

Monath, "Yellow Fever: an Update," *Lancet Infect. Dis.* 1:11-20, 2001.

Monath et al., "Clinical Proof of Principle for ChimeriVax™: Recombinant Live, Attenuated Vaccines Against Flavivirus Infections," Vaccine 20:1004-1018, 2002.

Monath et al., "Single Mutaion in the Flavivirus Envelope Protein Hinge Region Increases Neurovirulence for Mice and Monkeys but Decreases Viscerotropism for Monkeys: Relevance for Development and Safety Testing of Live, Attenuated Vaccines," *J. Virology* 76:1932-1943, 2002.

Morens and Halstead, "Measurement of Antibody-Dependent Infection Enhancement of Four Dengue Virus Serotypes by Monoclonal and Polyclonal Antibodies," *J. Gen. Virol.* 71(12):2909-2914, 1990.

Pervikov, "Development of Dengue Vaccine," W.H.O. Dengue Bulletin 24, 2000.

Pletnev et al., "Construction and Characterization of Chimeric Tick-Borne Encephalitis/Dengue Type 4 Viruses," *Proc. Natl. Acad. Sci. U.S.A.* 89:10532-10536, 1992.

Poildinger et al., "Molecular Characterization of the Japanese Encephalitis Serocomplex of the Flavivirus Genus," *Virology* 218:417-421, 1996.

Rey, "Dengue Virus Envelope Glycoprotein Structure: New Insight Into Its Interactions During Viral Entry," *Proc. Natl. Acad. Sci. U.S.A.* 100(12):6899-6901, 2003.

Rice et al., "Transcription of Infections Yellow Fever RNA from Full-Length cDNA Templates Produced by in Vitro Ligation," *New Biol.* 1:285-296, 1989.

Rothamn, "Dengue: Defining Protective Versus Pathologic Immunity," *J. Clin. Invest.* 113(7):948-951, 2004.

Ryman et al., "Yellow Fever Virus Envelope Protein has Two Discrete Type-Specific Neutralizing Epitopes," *J. Gen. Virology* 78:1353-1356, 1997.

Sabchareon et al., "Safety and Immunogenicity of Tetravalent Live-Attenuated Dengue Vaccines in Thai Adult Volunteers: Role of Serotype Concentration, Ratio, adn Multiple Doses," *Am. J. Trop. Med. Hyg.* 66:264-272, 2002.

Shiu et al., "Genomic Sequence of the Structural Proteins of Louping III Virus: Comparative Analysis with Tick-Borne Encephalitis Virus," *Virology* 180:411-415, 1991.

Stephenson, "Flavivirous Vaccines," *Vaccine* 6(6):471-480, 1988. Abstract only.

Stocks and Lobigs, "Signal Peptidase Cleavage at the Flavivirus C-prM Junction: Dependence on the Viral NS2B-3 Protease for Efficient Processing Requires Determinants in C, the Signal Peptide, and prM," *J. Virology* 72:2141-2149, 1998.

Sun et al., "Vaccination of Human Volunteers with Monovalent and Tetravalent Live-Attenuated Dengue Vaccine Candidates," *Am. J. Trop. Med. Hyg.* 69(Suppl 6):24-31, 2003.

Tesh et al., "Efficacy of Killed Virus Vaccine, Live Attenuated Chimeric Virus Vaccine, and Passive Immunization for Prevention of West Nile Virus Encephalitis in Hamster Model," *Emerg. Infect. Dis.* 8:1392-1397, 2002.

Theiler and Smith, "The Use of Yellow Fever Virus Modified by In Vitro Cultivation for Human Immunization," *Rev. Med. Virol.* 10:3-16, 2000.

Van Der Most et al., "Chimeric Yellow Fever/Dengue Virus as a Candidate Dengue Vaccine: Quantitation of the Dengue Virus-Specific CD8 T-Cell Response," *J. Virology* 74:8094-8101, 2000.

Venugopal and Gould, "Towards a New Generation of Flavivirus Vaccines," *Vaccine* 12:966-975, 1994.

Vlaycheva et al., "Yellow Fever 17D Virus: Pseudo-Revertant Suppression of Defective Virus Penetration and Spread by Mutations in Domains II and III of the E protein," *Virology* 327:41-49, 2004.

Volk et al., "Solution Structure and Antibody Binding Studies of the Envelope Protein Domain III from the New York Strain of West Nile Virus," *J. Biol. Chem.* 279:38755-38761, 2004.

Wang et al., "Comparison of the Genomes of the Wild-Type French Viscerotropic Strain of Yellow Fever Virus with Its Vaccine Derivative French Neurotropic Vaccine," *J. Gen. Virology* 76:2749-2755, 1995.

Yamshchikov et al., "An Attenuated West Nile Prototype Virus is Highly Immunogenic and Protects Against the Deadly NY99 Strain: A Candidate for Live WN Vaccine Developement," *Virology*, 330:304-312, 2004.

Yang et al., "Induction of Potent Th1-Type Immune Responses from a Novel DNA Vaccine for West Nile Virus New York Isolate (WNV-NY1999)," *J. Infect. Dis.* 184:809-816, 2001.

International Search Report from WO02/102828 dated Apr. 18, 2003.
International Search Report from WO03/063725 dated Jun. 25, 2003.
International Search Report from WO03/101397 dated Sep. 4, 2003.
International Search Report from WO03/103571 dated Dec. 12, 2003.
International Search Report from WO04/045529 dated Jun. 28, 2004.
International Search Report from WO05/082020 dated Sep. 30, 2005.
International Search Report from WO06/044857, dated May 30, 2006.
International Search Report from WO06/116182 dated Jul. 17, 2006.
European Search Report from European Application No. 05012770.
Supplemental European Search Report from European Application No. EP 03783570.
London et al., "Infectious Enveloped RNA Virus Antigenic Chimeras," Proc. Natl. Acad. Sci. USA 89:207-211, 1992.
Translation of Notice of Reasons for Rejection from Japanese Patent Application No. 2003-506300, dated Dec. 5, 2007.

* cited by examiner 1 2 3 4 5 6 7 8 9 10 11

1 2 3 4 5 6 7 8 9 10 11 12 13 14

CHIMERIC FLAVIVIRUS VECTORS

PRIORITY INFORMATION

This application claims priority from U.S. Provisional Application No. 60/295,265, filed Jun. 1, 2001.

FIELD OF THE INVENTION

This invention relates to chimeric flavivirus vectors and methods employing these vectors.

BACKGROUND OF THE INVENTION

Flaviviruses are small, enveloped positive-strand RNA viruses. Flavivirus proteins are produced by translation of a single, long open reading frame to generate a polyprotein, which is followed by a complex series of post-translational proteolytic cleavages of the polyprotein by a combination of host and viral proteases to generate mature viral proteins (Amberg et al., J. Virol. 73:8083-8094, 1999; Rice, "Flaviviridae," In *Virology*, Fields (ed.), Raven-Lippincott, New York, 1995, Volume I, p. 937). The virus structural proteins are arranged in the polyprotein in the order C-prM-E, where "C" is capsid, "prM" is a precursor of the viral envelope-bound M protein, and "E" is the envelope protein. These proteins are present in the N-terminal region of the polyprotein, while the non-structural proteins (NS1, NS2A, NS2B, NS3, NS4A, NS4B, and NS5) are located in the C-terminal region of the polyprotein.

A chimeric flavivirus that includes the C and non-structural proteins of the Yellow fever virus vaccine strain (YF 17D) and the prM and E proteins of a strain of attenuated Japanese encephalitis virus (SA 14-14-2) has been made. This chimera, designated CHIMERIVAX™-JE (chimeric flavivirus comprising capsid and non-structural proteins from yellow fever virus and pre-membrane and envelope proteins from Japanese encephalitis virus), has been shown to induce the production of neutralizing antibodies against JE in immunized rhesus monkeys, as well as to protect these monkeys from clinical encephalitis after JE challenge, as compared with unimmunized controls. CHIMERIVAX™-JE (chimeric flavivirus comprising capsid and non-structural proteins from yellow fever virus and pre-membrane and envelope proteins from Japanese encephalitis virus) was shown to meet preclinical safety requirements for a human vaccine (Monath et al., J. Virol. 74(4):1742-1751, 2000).

A similar chimera was made that includes the C and non-structural proteins of YF 17D and the prM and E proteins of a Dengue-2 strain. This chimera, designated CHIMERIVAX™-D2 (chimeric flavivirus comprising capsid and non-structural proteins from yellow fever virus and pre-membrane and envelope proteins from Dengue-2 virus), was shown to induce neutralizing antibodies against Dengue-2 virus in rhesus monkeys, as well as to protect these monkeys from viremia after Dengue-2 challenge, as compared with unimmunized controls. CHIMERIVAX™-D2 (chimeric flavivirus comprising capsid and non-structural proteins from yellow fever virus and pre-membrane and envelope proteins from Dengue-2 virus) also was shown to be safe and genetically stable (Guirakhoo et al., J. Virol. 74(12):5477-5485, 2000).

SUMMARY OF THE INVENTION

The invention provides methods for identifying sites in the envelope proteins of chimeric flaviviruses or genetically attenuated flaviviruses that are permissive for insertion of foreign peptides. These methods include the steps of: (i) introducing a nucleic acid molecule encoding a foreign peptide into a gene encoding a flavivirus envelope protein; (ii) generating a flavivirus vector including an envelope protein encoded by the gene, wherein the envelope protein contains the foreign peptide; and (iii) determining whether the flavivirus vector generated in step (ii) is permissive for the insertion.

The flavivirus vectors can be chimeric flavivirus vectors that include, for example, the C and non-structural proteins of a first flavivirus and the prM and E proteins of a second flavivirus. The first and second flaviviruses can be selected from the group consisting of Japanese encephalitis, Dengue (serotype 1, 2, 3, or 4), Yellow fever (e.g., YF 17D), Murray Valley encephalitis, St. Louis encephalitis, West Nile, Kunjin, Rocio encephalitis, Ilheus, ticke-borne encephalitis, Central European encephalitis, Siberian encephalitis, Russian Spring-Summer encephalitis, Kyasanur Forest Disease, Omsk Hemorrhagic fever, Louping ill, Powassan, Negishi, Absettarov, Hansalova, Apoi, and Hypr viruses.

The foreign peptides inserted into the vectors of the invention can include epitopes derived from, for example, antigens of viral, bacterial, or parasitic pathogens, or can include epitopes derived from tumor-associated antigens. Examples of these peptides and others are provided below.

The nucleic acid molecules can be introduced into the envelope genes of the flaviviruses, according to the methods of the invention, for example, randomly by transposon mutagenesis. Also, determination of whether the flavivirus vectors generated in step (ii) of the methods of the invention are permissive for the insertion can be carried out, for example, by analysis of (a) the infectivity of the flavivirus vectors, (b) the stability of the sequence of the foreign protein upon multiple passages of the vectors, (c) the growth properties of the flavivirus vectors, and/or (d) whether the flavivirus vectors can be neutralized with antibodies against the envelope protein of the first flavivirus. The methods of the invention can further include comparing the analysis of the flavivirus vectors with a similar analysis of the flavivirus from which it was derived.

The invention also includes flavivirus vectors that include envelope proteins that contain foreign peptides. The flavivirus vectors can be chimeric flaviviruses including the prM and E proteins of a first flavivirus and the C and non-structural proteins of a second flavivirus. The first and second flaviviruses can be selected from the group consisting of Japanese encephalitis, Dengue (serotype 1, 2, 3, or 4), Yellow fever (e.g., YF 17D), Murray Valley encephalitis, St. Louis encephalitis, West Nile, Kunjin, Rocio encephalitis, Ilheus, ticke-borne encephalitis, Central European encephalitis, Siberian encephalitis, Russian Spring-Summer encephalitis, Kyasanur Forest Disease, Omsk Hemorrhagic fever, Louping ill, Powassan, Negishi, Absettarov, Hansalova, Apoi, and Hypr viruses. The flavivirus vectors can, alternatively, be a genetically attenuated flavivirus, such as Yellow Fever YF 17D.

The foreign peptides inserted into the vectors can include epitopes derived from antigens of viral, bacterial, or parasitic pathogens. Alternatively, the foreign peptides can include epitopes derived from tumor-associated antigens.

Also included in the invention are pharmaceutical compositions that include the flavivirus vectors described above and pharmaceutically acceptable carriers or diluents, as well as methods of delivering peptides to patients by administering to the patients such compositions. These methods can be carried out, for example, when the peptides are antigens, to induce an immune response to pathogens or tumors from which the antigens are derived.

The invention also includes nucleic acid molecules that include the genomes of the flaviviruses described above or the complements thereof.

The invention provides several advantages. For example, chimeric flavivirus vectors that can be used in the invention are sufficiently attenuated so as to be safe, and yet are able to induce protective immunity to the flaviviruses from which the envelope proteins in the chimeras are derived and, in particular, the epitopes inserted into the chimeras. Additional safety comes from the fact that the vectors used in the invention are chimeric, thus eliminating the possibility of reversion to wild type. An additional advantage of the vectors used in the invention is that flaviviruses replicate in the cytoplasm of cells, so that the virus replication strategy does not involve integration of the viral genome into the host cell, providing an important safety measure. In addition, as is discussed further below, a single vector of the invention can be used to deliver multiple epitopes from a single antigen, or epitopes derived from more than one antigen.

Other features and advantages of the invention will be apparent from the following detailed description, the drawings, and the claims.

DETAILED DESCRIPTION

Figure 1:
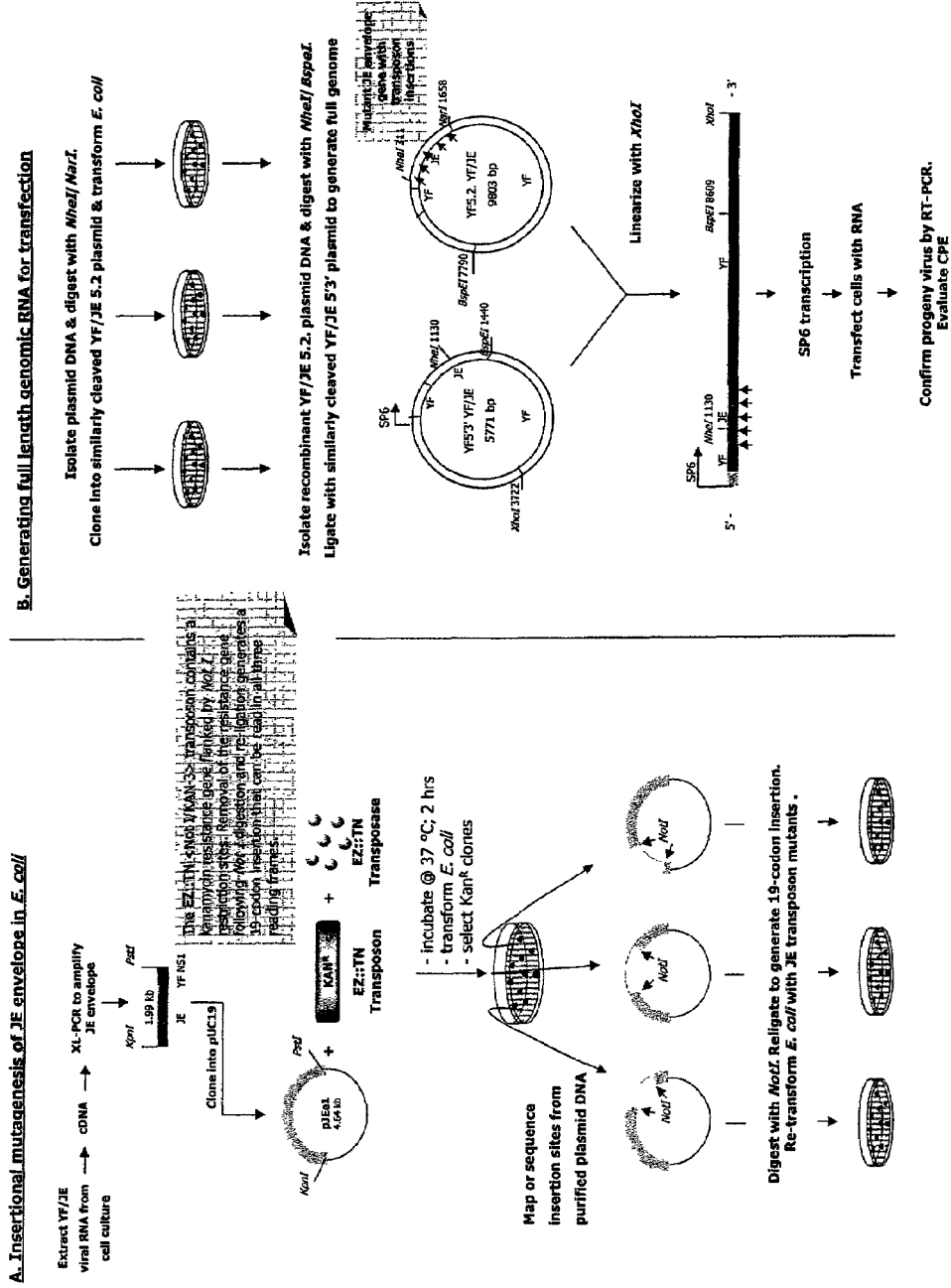
FIG. 1 is a schematic representation of a transposon mutagenesis method carried out with the gene encoding the JE envelope.

The invention provides methods of identifying sites in the envelope proteins of chimeric flaviviruses or genetically attenuated flaviviruses (e.g., YF 17D) into which foreign peptides can be introduced, chimeric flavivirus vectors having envelope proteins that include such peptides, and methods of delivering these peptides by administration of the vectors in order to, for example, induce an immune response to a pathogen from which an introduced peptide is derived. Details of these vectors, peptides, and methods are provided below.

Chimeric Flavivirus Vectors

Chimeric viruses that can be used in the invention consist of a first flavivirus (i.e., a backbone flavivirus) in which a structural protein (or proteins) has been replaced with a corresponding structural protein (or proteins) of a second virus. For example, the chimeras can consist of a first flavivirus in which the prM and E proteins have been replaced with the prM and E proteins of a second virus.

The chimeric viruses that are used in the invention can be made from any combination of viruses. Examples of particular flaviviruses that can be used in the invention, as first or second viruses, include mosquito-borne flaviviruses, such as Japanese encephalitis, Dengue (serotypes 1-4), Yellow fever, Murray Valley encephalitis, St. Louis encephalitis, West Nile, Kunjin, Rocio encephalitis, and Ilheus viruses; tick-borne flaviviruses, such as Central European encephalitis, Siberian encephalitis, Russian Spring-Summer encephalitis, Kyasanur Forest Disease, Omsk Hemorrhagic fever, Louping ill, Powassan, Negishi, Absettarov, Hansalova, Apoi, and Hypr viruses; as well as viruses from the Hepacivirus genus (e.g., Hepatitis C virus).

Details of making chimeric viruses that can be used in the invention are provided, for example, in U.S. patent application Ser. Nos. 09/007,664, 09/121,587, and 09/452,638; International applications PCT/US98/03894 and PCT/US00/32821; and Chambers et al., J. Virol. 73:3095-3101, 1999, each of which is incorporated by reference herein in its entirety.

A specific example of a type of chimeric virus that can be used in the invention is the yellow fever human vaccine strain, YF 17D, in which the prM and E proteins have been replaced with prM and E proteins of another flavivirus, such as Japanese encephalitis virus, West Nile virus, St. Louis encephalitis virus, Murray Valley encephalitis virus, a Dengue virus, or any other flavivirus, such as one of those listed above. For example, the following chimeric flaviviruses, which were deposited with the American Type Culture Collection (ATCC) in Manassas, Va., U.S.A. under the terms of the Budapest Treaty and granted a deposit date of Jan. 6, 1998, can be used in the invention: Chimeric Yellow Fever 17D/Japanese Encephalitis SA14-14-2 Virus (YF/JE A1.3; ATCC accession number ATCC VR-2594) and Chimeric Yellow Fever 17D/Dengue Type 2 Virus (YF/DEN-2; ATCC accession number ATCC VR-2593).

Methods for Identifying Permissive Sites in Chimeric Flavivirus Envelope Proteins Sites in chimeric flavivirus envelope proteins that are permissive to insertion of foreign sequences can be identified as follows. Nucleic acid sequences encoding a peptide are inserted into the envelope gene using standard methods of molecular biology. Preferably, such nucleic acid sequences are randomly inserted into the envelope gene, to facilitate the creation of a library of insertion mutants. However, a nucleic acid sequence can, alternatively, be inserted a specific point in an envelope gene and tested for efficacy. The latter approach may be desirable, for example, when a particular site has been identified as being permissive for insertion of a first foreign sequence and it is desired to confirm that it is also permissive for insertion of a second sequence that may, for example, differ in length or predicted secondary structure from the first foreign sequence.

Random insertion of nucleic acid sequences can be achieved, for example, by the use of a transposon mutagenesis approach. For example, a Tn5 transposition system can be used (Goryshin et al., J. Biol. Chem. 273:7367, 1998). As a specific example, the EZ::TN Insertion System, which is manufactured by Epicentre Technologies (Madison, Wis., U.S.A.), can be used. Details of the use of this system in the invention are provided further below. In summary, a cloned flavivirus envelope gene is subjected to mutagenesis with transposons that include sequences that encode peptides. A library of mutants that include randomly integrated transposons in flavivirus envelope genes is generated and, if desired, the insertion sites are mapped and/or sequenced. Full length genomic RNA that includes mutant envelope genes is then generated and used to make mutant viruses, which are then characterized for permissiveness to insertion of the transposons. The viruses can be analyzed for permissiveness by, for example, determination of infectivity, genomic stability, growth properties, and neutralization. Details of the use of this transposon mutagenesis system are provided below, in the context of the chimeric flavivirus CHIMERIVAX™-JE (chimeric flavivirus comprising capsid and non-structural proteins from yellow fever virus and pre-membrane and envelope proteins from Japanese encephalitis virus) (also see FIG. 1). However, the methods can be used with any of the chimeras described herein.

Foreign Peptides

The vectors of the invention can be used in the delivery of any peptide or protein of prophylactic or therapeutic value. For example, the vectors of the invention can be used in the induction of an immune response (prophylactic or therapeutic) to any protein-based antigen that is inserted into a chimeric flavivirus envelope protein. Preferably, such an antigen not derived from the second flavivirus of the chimera. All that is required is that a nucleic acid sequence encoding the antigen be inserted at a permissive site within the envelope gene of a chimeric flavivirus, as described herein. Standard methods of molecular biology can be used to insert the antigen-coding nucleic acid molecules into chimera envelope genes, at permissive sites, which are identified as is described elsewhere herein.

The vectors of the invention can each include a single epitope. Alternatively, multiple epitopes can be inserted into the vectors, either at a single site (i.e., as a polytope, in which the different epitopes can be separated by a flexible linker, such as a polyglycine stretch of amino acids), at different sites, or in any combination thereof. The different epitopes can be derived from a single species of pathogen, or can be derived from different species and/or different genuses.

Antigens that can be used in the invention can be derived from, for example, infectious agents such as viruses, bacteria, and parasites. For example, antigens from the pathogens listed in Table 2, below, can be used. Specific examples of such antigens include those listed in Table 3. In addition, specific examples of epitopes that can be inserted into the vectors of the invention are provided in Table 4. As is noted in Table 4, epitopes that are used in the vectors of the invention can be B cell epitopes (i.e., neutralizing epitopes) or T cell epitopes (i.e., T helper and cytotoxic T cell-specific epitopes).

The vectors of the invention can be used to deliver antigens in addition to pathogen-derived antigens. For example, the vectors of the invention can be used to deliver tumor-associated antigens for use in immunotherapeutic methods against cancer. Numerous tumor-associated antigens are known in the art and can be used in the invention. Examples of cancers (and corresponding tumor associated antigens) are as follows: melanoma (NY-ESO-1 protein (specifically CTL epitope located at amino acid positions 157-165), CAMEL, MART 1, gp100, tyrosine-related proteins TRP1 and 2, and MUC1)); adenocarcinoma (ErbB2 protein); colorectal cancer (17-1A, 791Tgp72, and carcinoembryonic antigen); prostate cancer (PSA1 and PSA3). Heat shock protein (hspp110) can also be used as such an antigen.

In another embodiment of the invention, exogenous proteins that encode an epitope(s) of an allergy-inducing antigen to which an immune response is desired may be used. In addition, the vectors of the invention can include ligands that are used to target the vectors to deliver peptides, such as antigens, to particular cells (e.g., cells that include receptors for the ligands) in subjects to whom the vectors administered.

The size of the peptide or protein that is inserted into the vectors of the invention can range in length from, for example, from 5-500 amino acids in length, for example, from 10-100, 20-55, 25-45, or 35-40 amino acids in length. The feasibility of using any particular desired peptide can easily be determined using the methods described herein.

Use of Chimeric Flavivirus Vectors to Deliver Foreign Peptides

The vectors of the invention are administered in amounts and by using methods that can readily be determined by persons of ordinary skill in this art. The vectors can be administered and formulated, for example, in the same manner as the yellow fever 17D vaccine, e.g., as a clarified suspension of infected chicken embryo tissue, or a fluid harvested from cell cultures infected with the chimeric yellow fever virus. Thus, the vectors of the invention can be formulated as sterile aqueous solutions containing between 100 and 1,000,000 infectious units (e.g., plaque-forming units or tissue culture infectious doses) in a dose volume of 0.1 to 1.0 ml, to be administered by, for example, intramuscular, subcutaneous, or intradermal routes. In addition, because flaviviruses may be capable of infecting the human host via the mucosal routes, such as the oral route (Gresikova et al., "Tick-borne Encephalitis," In *The Arboviruses, Ecology and Epidemiology*, Monath (ed.), CRC Press, Boca Raton, Fla., 1988, Volume IV, 177-203), the vectors can be administered by a mucosal route.

When used in immunization methods, the vectors can be administered as a primary prophylactic agent in adults or children at risk of infection by a particular pathogen. The vectors can also be used as secondary agents for treating infected patients by stimulating an immune response against the pathogen from which the peptide antigen is derived.

For vaccine applications, adjuvants that are known to those skilled in the art can be used. Adjuvants that can be used to enhance the immunogenicity of the chimeric vectors include, for example, liposomal formulations, synthetic adjuvants, such as (e.g., QS21), muramyl dipeptide, monophosphoryl lipid A, or polyphosphazine. Although these adjuvants are typically used to enhance immune responses to inactivated vaccines, they can also be used with live vaccines. In the case of a chimeric vector delivered via a mucosal route, for example, orally, mucosal adjuvants such as the heat-labile toxin of *E. coli* (LT) or mutant derivations of LT can be used as adjuvants. In addition, genes encoding cytokines that have adjuvant activities can be inserted into the vectors. Thus, genes encoding cytokines, such as GM-CSF, IL-2, IL-12, IL-13, or IL-5, can be inserted together with foreign antigen genes to produce a vaccine that results in enhanced immune responses, or to modulate immunity directed more specifically towards cellular, humoral, or mucosal responses.

In addition to vaccine applications, as one skilled in the art can readily understand, the vectors of the invention can be used in gene therapy methods to introduce therapeutic gene products into a patient's cells and in cancer therapy. In these methods, genes encoding therapeutic gene products are inserted into permissive sites in the vectors.

EXAMPLE

The following experimental example shows the identification of permissive sites in CHIMERIVAX™-JE (chimeric flavivirus comprising capsid and non-structural proteins from yellow fever virus and pre-membrane and envelope proteins from Japanese encephalitis virus). The methods described in this example can be used with other chimeric flaviviruses, such as those described above, as well.

The Yellow fever 17D (YF 17D) live attenuated vaccine strain has been used in humans for the past 60 years, has an excellent safety record, and provides long-lasting immunity after administration of a single dose. As is noted above, CHIMERIVAX™-JE (chimeric flavivirus comprising capsid and non-structural proteins from yellow fever virus and pre-membrane and envelope proteins from Japanese encephalitis virus) is a live, attenuated recombinant vaccine strain in which the genes encoding the structural proteins (PrME) of YF 17D have been replaced with the corresponding genes from the genetically attenuated Japanese encephalitis (JE) virus SA14-14-2. Both capsid and all nonstructural (NS) genes responsible for intracellular replication of this chimera are derived from the YF 17D vaccine strain. As is noted above, an infectious molecular clone of CHIMERIVAX™-JE (chimeric flavivirus comprising capsid and non-structural proteins from yellow fever virus and pre-membrane and envelope proteins from Japanese encephalitis virus) (YF/JE) has previously been described. In the experiments described below, CHIMERIVAX™-JE (chimeric flavivirus comprising capsid and non-structural proteins from yellow fever virus and pre-membrane and envelope proteins from Japanese encephalitis virus) was evaluated as to its suitability as a delivery vehicle for biologically relevant peptides.

The EZ::TN In-Frame Linker Insertion Kit© (Epicentre) is a fast and efficient method for randomly inserting 19 amino acid peptides in-frame into proteins encoded by cloned DNA for a variety of applications. Using this approach, we have chosen to identifying sites within the envelope gene of CHIMERIVAX™-JE (chimeric flavivirus comprising capsid and non-structural proteins from yellow fever virus and pre-membrane and envelope proteins from Japanese encephalitis virus) that are permissive to foreign DNA. As is discussed in further detail below, random mutagenesis in *E. coli* of the gene encoding the JE envelope protein with EZ::TN identified a bank of stable insertion mutants that carried the 57 basepairs fragment that encodes the 19 amino acid peptide. DNA sequence analysis, restriction mapping, and PCR studies confirmed both the exact location of the transposon and the random nature of insertion. Engineering the mutated JE envelope gene back into the CHIMERIVAX™-JE (chimeric flavivirus comprising capsid and non-structural proteins from yellow fever virus and pre-membrane and envelope proteins from Japanese encephalitis virus) infectious clone has allowed us to study infection in cell culture and provide valuable information on the use of recombinant flaviviruses as delivery vehicles for foreign antigens. We identified a panel of mutant clones infectious for Vero cells and characterized their biological properties. Specifically, we compared the growth properties of stable infectious clones to the parental CHIMERIVAX™-JE (chimeric flavivirus comprising capsid and non-structural proteins from yellow fever virus and pre-membrane and envelope proteins from Japanese encephalitis virus) chimera in cell culture, as well as their ability to be neutralized in a plaque reduction neutralization test (PRNT) with JE-specific polyclonal antisera. We identified sites within the JE envelope that are permissive to insertion of foreign DNA, and these sites can be exploited for delivery of biologically relevant epitopes. Further details are provided as follows.

Cloning of the Gene Encoding the JE Envelope into pUC19

YF/JE viral RNA was extracted from infected Vero cells using Trizol reagent (Gibco BRL). Following cDNA synthesis with the FNOR antisense primer (see below), the gene encoding the JE SA14-14-2 envelope was amplified by XL-PCR with TN1.F/TN2.R primers (see below), and directionally cloned by conventional methods into pUC19 (New England Biologicals, NEB, U.S.A.) using KpnI and PstI recognition sequences incorporated at the 5' ends of each oligonucleotide, generating pJEe1. PCR was carried out using a GeneAmp PCR System 2400 (Perkin Elmer).

Transposon Mutagenesis and Mapping of Insertion Sites

Insertion mutagenesis was performed on pJEe1 using the EZ::TN™ In-Frame Linker Insertion Kit (EPICENTRE Technologies, U.S.A.), according to manufacturer's instructions. The EZ::TN <NotI/Kan-3> transposon contains a kanamycin resistance gene flanked by Not I restriction sites. As is discussed further below, removal of the kanamycin resistance gene following NotI digestion and re-ligation generates a 19 codon insertion that can be read in all three reading frames.

Figure 2:
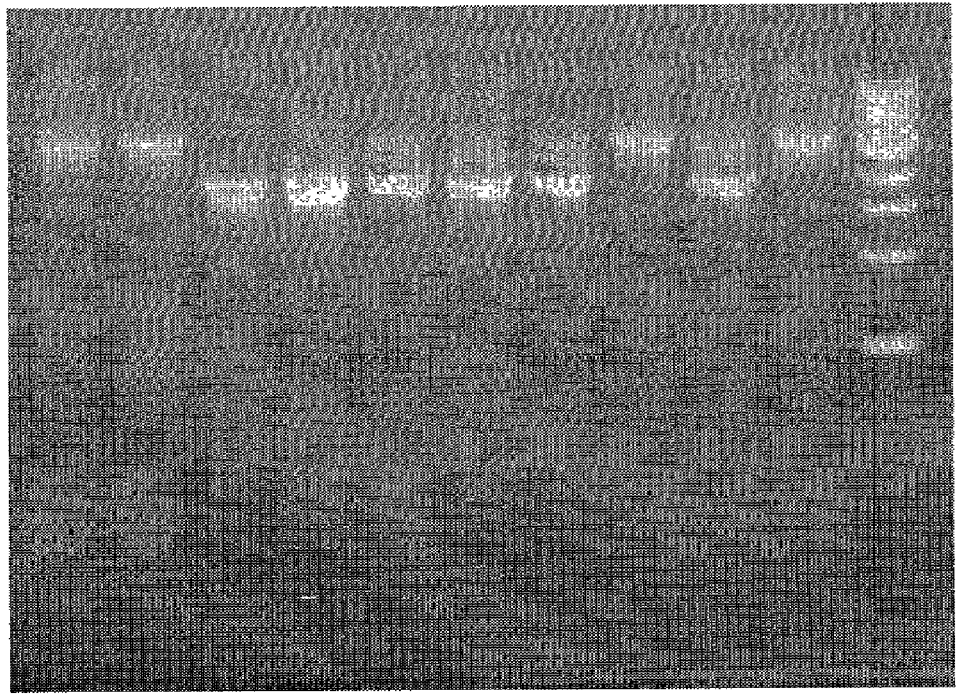
FIG. 2 shows the results of PCR analysis of Tn5 insertion mutants of the gene encoding the JE envelope. Stable clones harboring a transposon in the JE envelope are shown in lanes 1, 2, 8, and 10; clones harboring a transposon within the pUC19 vector are shown in lanes 3 and 4; unstable clones harboring a transposon in the JE envelope are shown in lanes 5-7 and 9; and a 1 kilobase marker is shown in lane 11.
Figure 3:
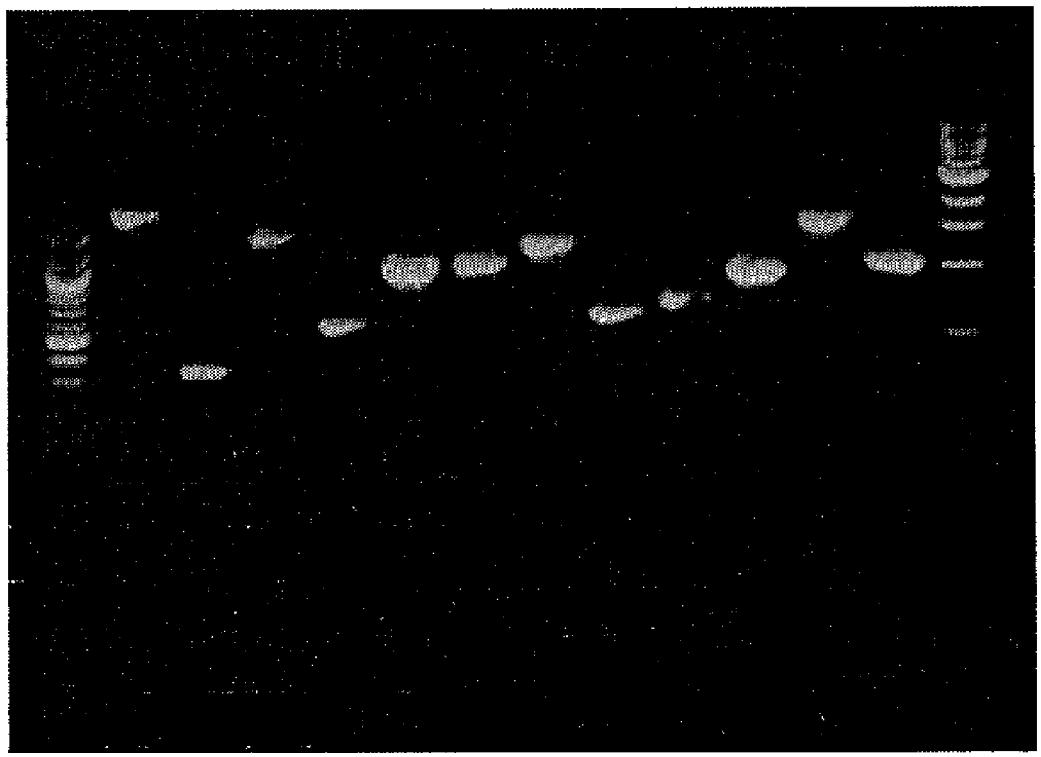
FIG. 3 shows the results of PCR mapping of select mutant plasmids. This analysis confirmed the random nature of the insertion into the JE envelope. Lanes 1-13 show the PCR products of 13 clones, while lane 14 contains a 1 kilobase marker.

Insertion mutants were identified in E. coli by selection on LB agar plus kanamycin (50 µg/ml). PCR with TN1.F/TN2.R on select kanamycin-resistant clones following transposition revealed that 40% of clones stably maintained the transposon in the JE envelope (FIG. 2). Insertion sites were mapped by PCR (Pwo DNA Polymerase, Boehringer Mannheim/Roche) using Tn5-specific primers TN1.F and NotI/KAN-3 RP-2, which showed that the Tn5 transposon inserted randomly into the JE envelope (FIG. 3). Unique clones were selected for sequencing and generation of full length mutant genomic RNA.

Sequencing

Figure 4:
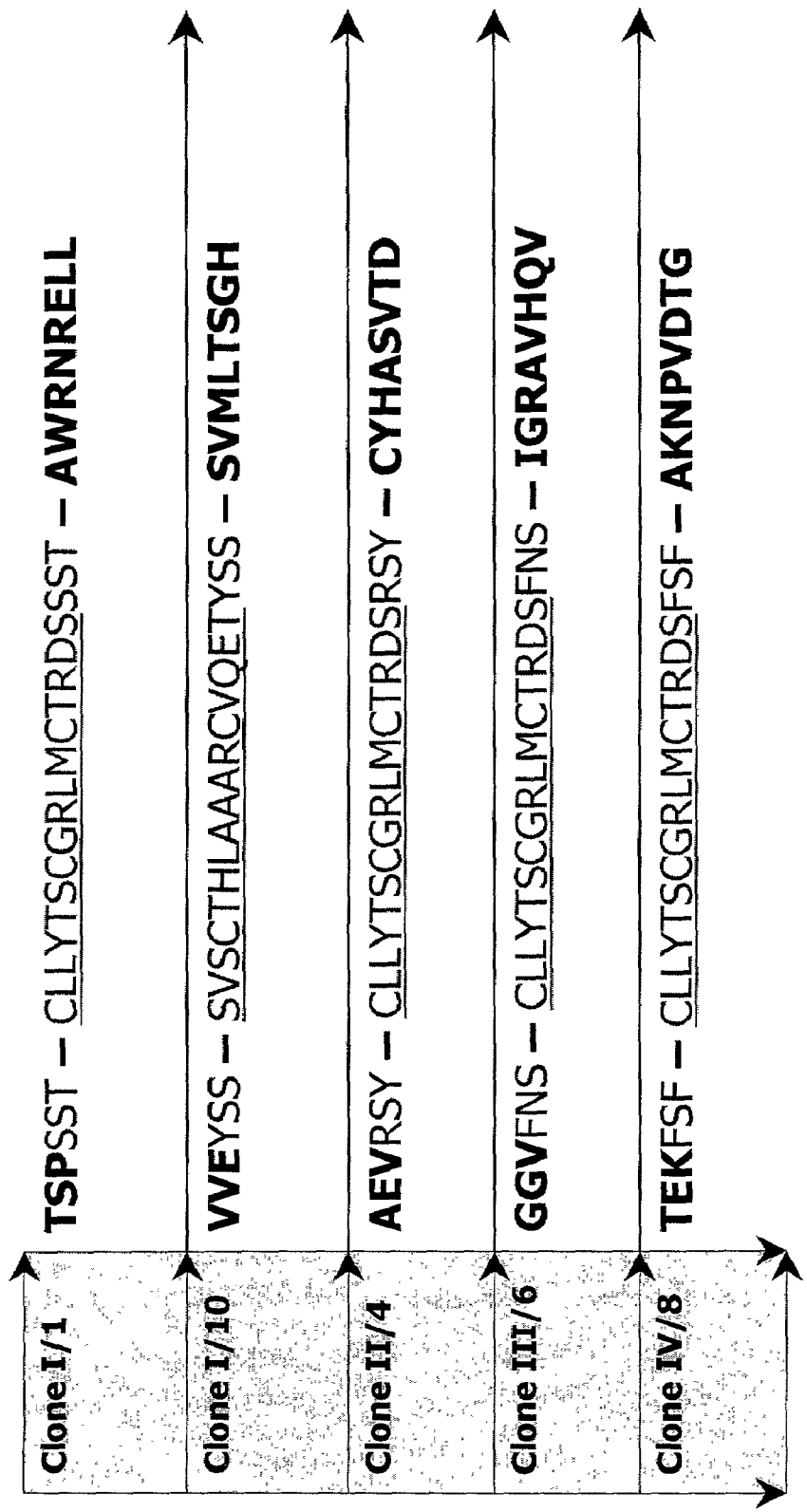
FIG. 4 shows the amino acid sequences of five mutant clones that were selected for transfection of Vero cells (Clone I/1 (SEQ ID NO:1); Clone I/10 (SEQ ID NO:2); Clone II/4 (SEQ ID NO:3); Clone III/6 (SEQ ID NO:4); and Clone IV/8 (SEQ ID NO:5). The JE envelope sequences are in boldface and the insert sequences following transposition are underlined. The remaining sequences, which are repeated sets of three amino acids each that are on the left side of the first dash and on the left side of the second dash in each line, are artifacts of the transposon mutagenesis.
Figure 5:
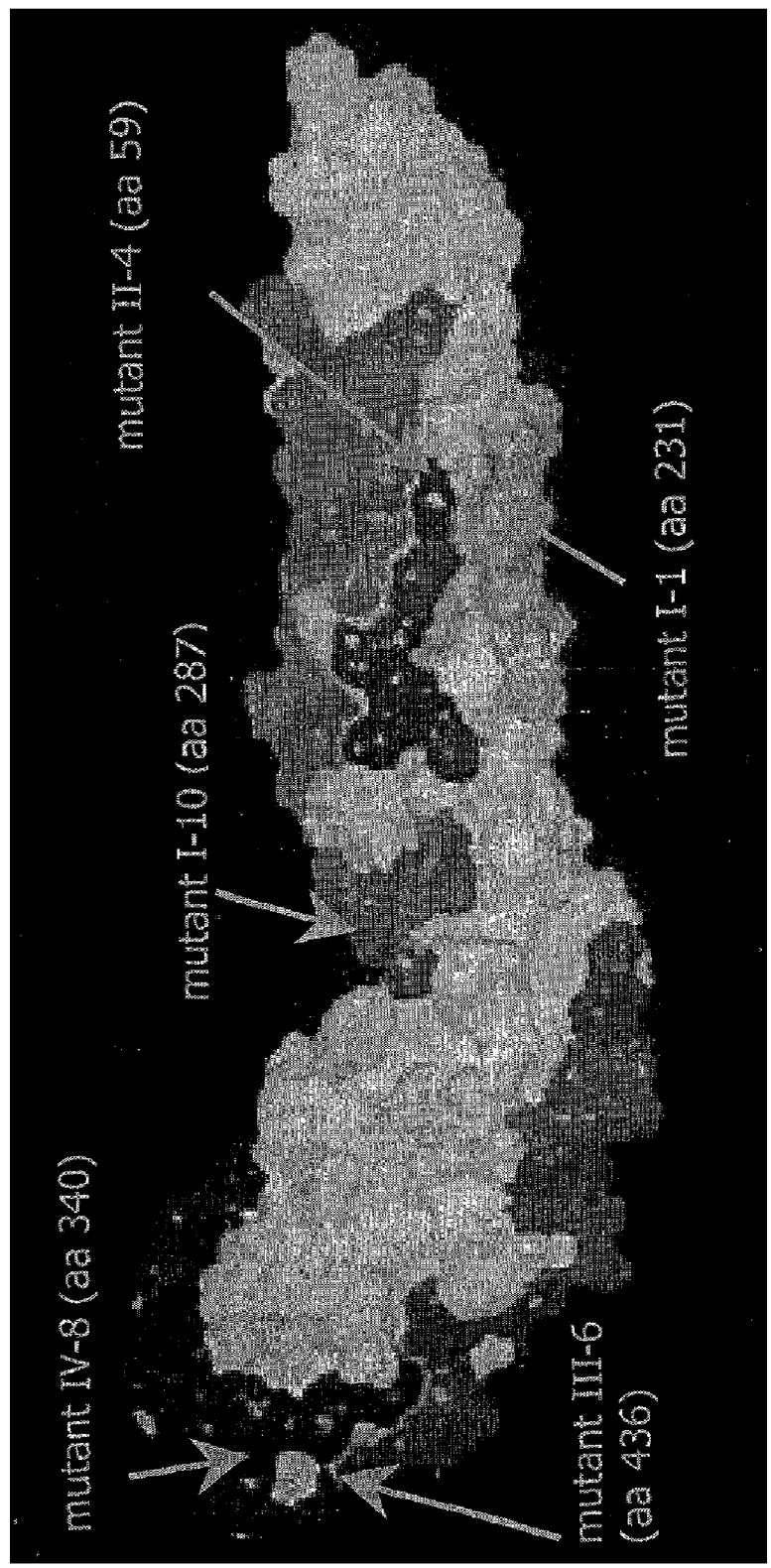
FIG. 5 is a schematic representation of the envelope glycoprotein of JE, which shows the locations of inserts relative to defined conformational epitopes of the protein. The arrows pinpoint the approximate insertion sites for 5 independent JE envelope mutants that were selected for transfection of Vero cells. The numbers in brackets indicate the JE envelope amino acid that precedes the 19 amino acid insert.

The amino acid sequences of five mutant clones that were selected for transfection of Vero cells is shown in FIG. 4. The locations of the inserts relative to defined conformation epitopes on the envelope protein of JE virus is shown in FIG. 5. The insertion sites were determined by DNA sequencing, and inserts were located by comparison to a predicted 3D structure of the JE envelope (Kolaskar et al., Virology 261: 31-42, 1999). Four of the five insertion sites appear to be surface exposed. Sequencing was performed using a CEQ™ 2000 DNA Analysis system (Beckman Coulter) and a CEQ 2000 Dye Terminator Cycle Sequencing Kit. Data were analyzed using SEQUENCHER™, Version 4.0.5. (Gene Codes Corporation).

Constructing Infectious Clones Harboring Tn5 Insertions

The antibiotic resistance marker was removed from stable E. coli clones, which were then re-ligated, leaving a 57 basepair in-frame insertion that included a 9-basepair target site sequence duplication that flanks the transposon. Sample clones (n=5) containing re-ligated JE envelope were then digested with NheI/NarI (NEB, U.S.A.), to be compatible for cloning into a two plasmid system previously described for generating full length YF/JE genomes (Chambers et al., 1999, supra).

Transcription and Transfection

Transcription of linearized, full length genomic DNA harboring foreign DNA in the gene encoding the JE envelope was performed from the SP6 promoter using the AmpliScribe™ SP6 High Yield Transcription Kit (EPICENTRE Technologies). Six well plates seeded with Vero cells were transfected with in vitro transcribed genomic RNA in the presence of LIPOFECTIN Reagent (Life Technologies) and maintained in MEM (Life Technologies) supplemented with 5% FBS (Hyclone), NEAA (Life Technologies), and 1% Penicillin-Streptomycin (Sigma Chemicals). Cell supernatants (500 mL) were passaged to fresh cells every 6 days through P6, and the monolayer was monitored for cytopathic effects (CPE). Viral RNA was extracted from the cell monolayer and supernatant at each passage.

Figure 6:
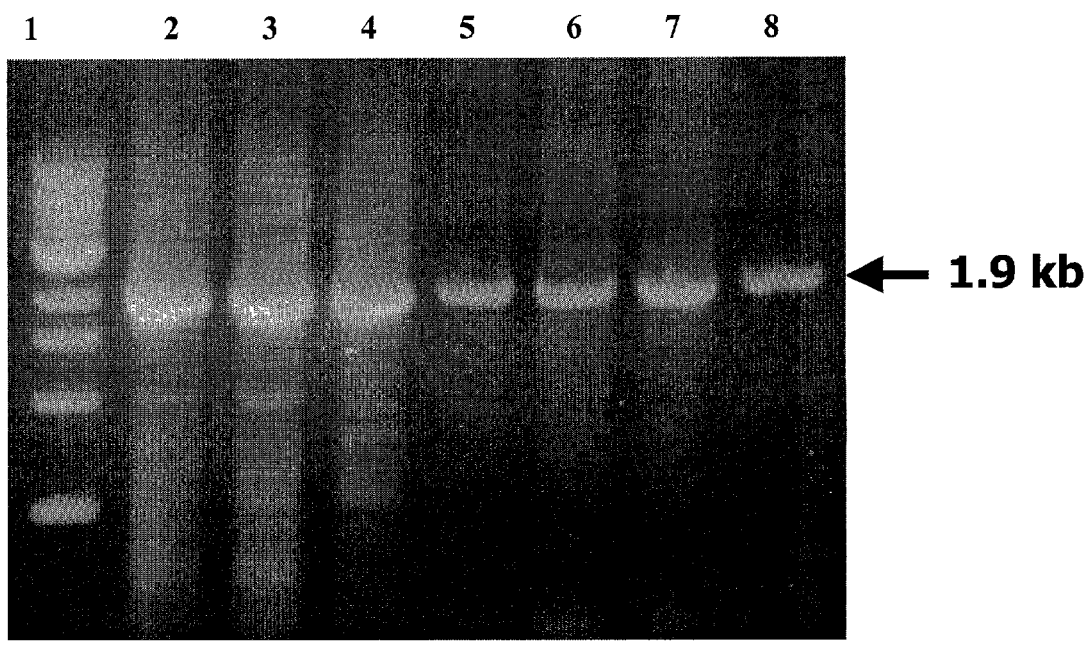
FIG. 6 shows the results of RT-PCR analysis of cDNA synthesized from RNA extracted from Vero cells that have been transfected with RNA made from 5 unique clones (2 in duplicate). A 1.9 kilobase insert that includes the 57 basepair linker was amplified from each of the clones, and confirms the production of progeny virus. A 1 kilobase marker is fractionated in lane 1. Lanes 2-8 correspond to clone I-10-2, clone I-10-3, clone II-4-3, clone II-4-6, clone I-1, clone III-6, and clone IV-8-1, respectively.
Figure 7:
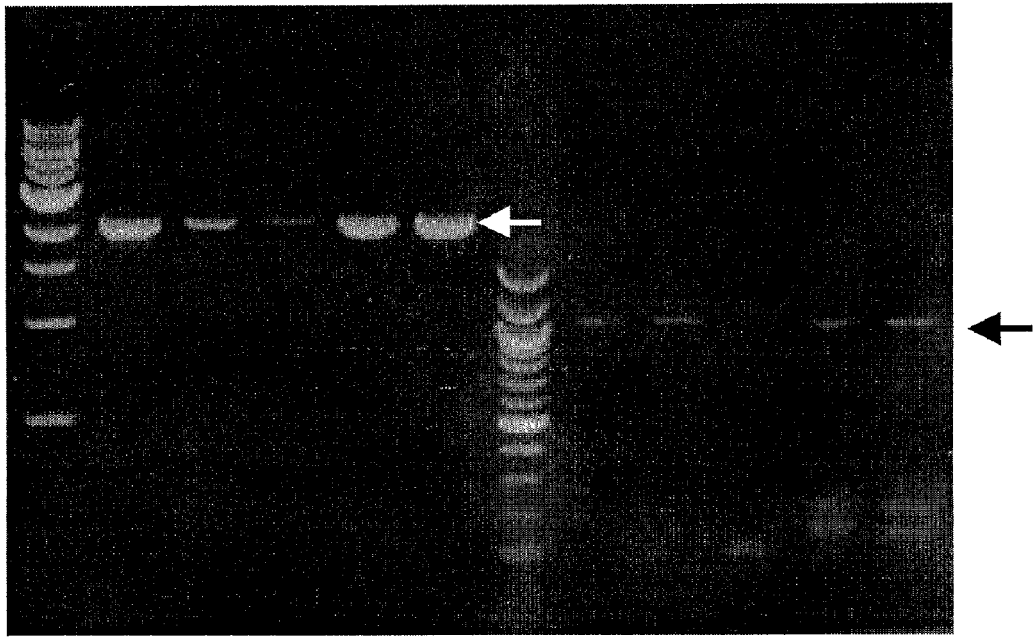
FIG. 7 shows the results of PCR analysis of clone I-10 cDNA at P2 through P6 (lanes 2-6 and 8-12, respectively). The samples fractionated on the left panel were obtained using JE envelope specific primers, while the samples fractionated on the right panel were obtained using a transposon-specific primer. A 1 kilobase marker is fractionated in lane 1 and a 100 basepair marker is fractionated in lane 7.

As is shown in FIG. 6, all mutant clones were infectious for Vero cells at P2. In particular, RT-PCR using TN1.F/TN2.R on cDNA synthesized from RNA extracts of cell monolayers amplified a 1.9 kilobase insert that harbors the 57 basepair linker, and confirms the production of progeny virus. PCR analysis of clone I-10 from P2 through P6 shows that this clone is stable through P6, and that its insertion site, at amino acid 287, is permissive for the insertion of foreign DNA. PCR was carried out with JE envelope gene-specific primers (TN1.F/TN2.R) and a transposon-specific primer (TN1.F/TMOS.R) (FIG. 7).

Figure 8:
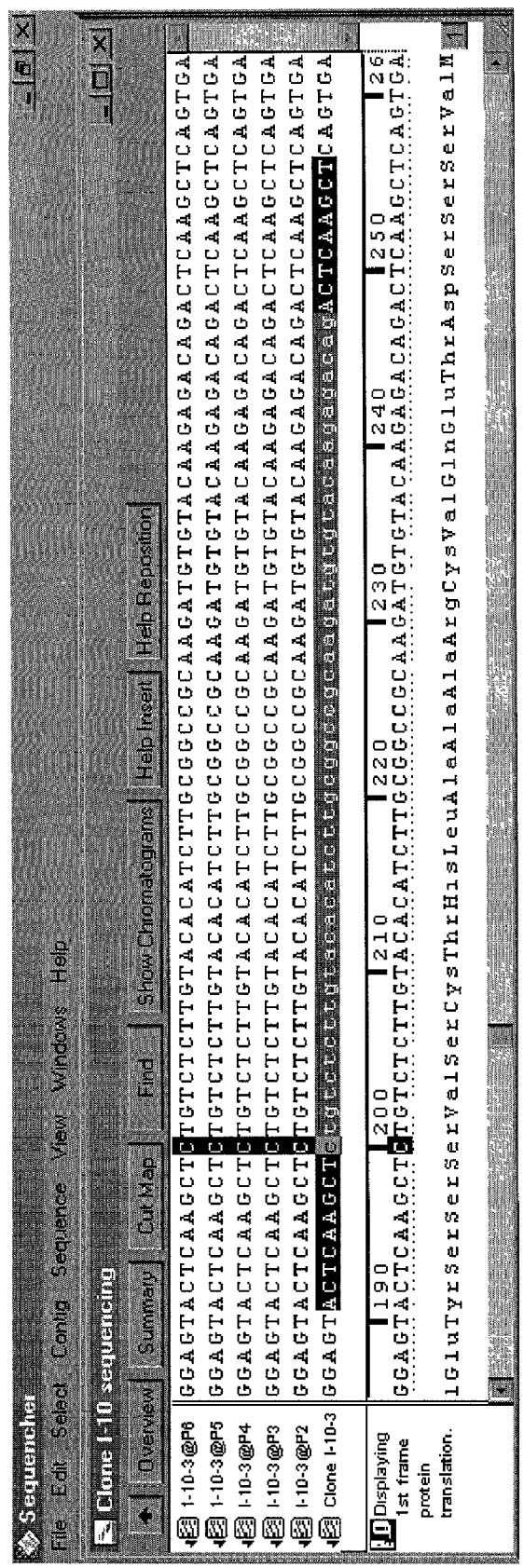
FIG. 8 shows the nucleotide sequences of the RT-PCR products of infectious clone I-10 at P2 through P6, aligned with the plasmid I-10 sequence prior to transfection (SEQ ID NO:6), and the corresponding amino acid sequence (SEQ ID NO:7). The arrows indicate two cysteine residues in the insert that have the potential to form a disulfide bond, possibly stabilizing the peptide on the envelope protein and presenting it on the surface of the molecule.
Figure 9:
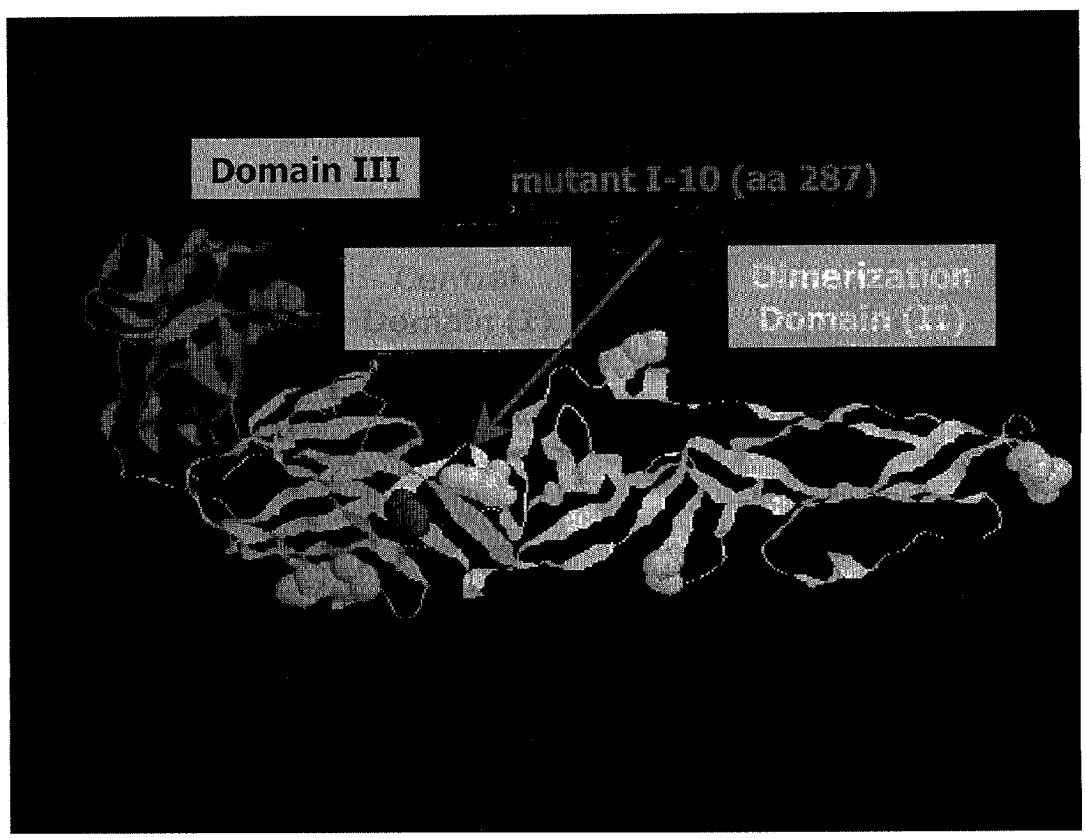
FIG. 9 is a schematic representation of the 3-dimensional structure of the JE envelope glycoprotein, showing that the permissive site at amino acid position 287 is located between the central (I) and the dimerization (II) domains, and appears to be surface exposed.

The DNA sequence of RT PCR products from P2 through P6 was determined and, as is shown in FIG. 8, the sequences at each passage were identical to the sequence of the original clone, I-10. Interestingly, the I-10 transposon insert contains two cysteine residues that have the potential to form a disulfide bond, which possibly stabilizes the foreign peptide on the envelope protein and presents it on the surface of the molecule. FIG. 9 depicts a 3-D structure of the JE virus envelope glycoprotein, and shows that position 287 is located between the central (I) domain and the dimerization (II) domain and appears to be surface exposed.

Figure 10:
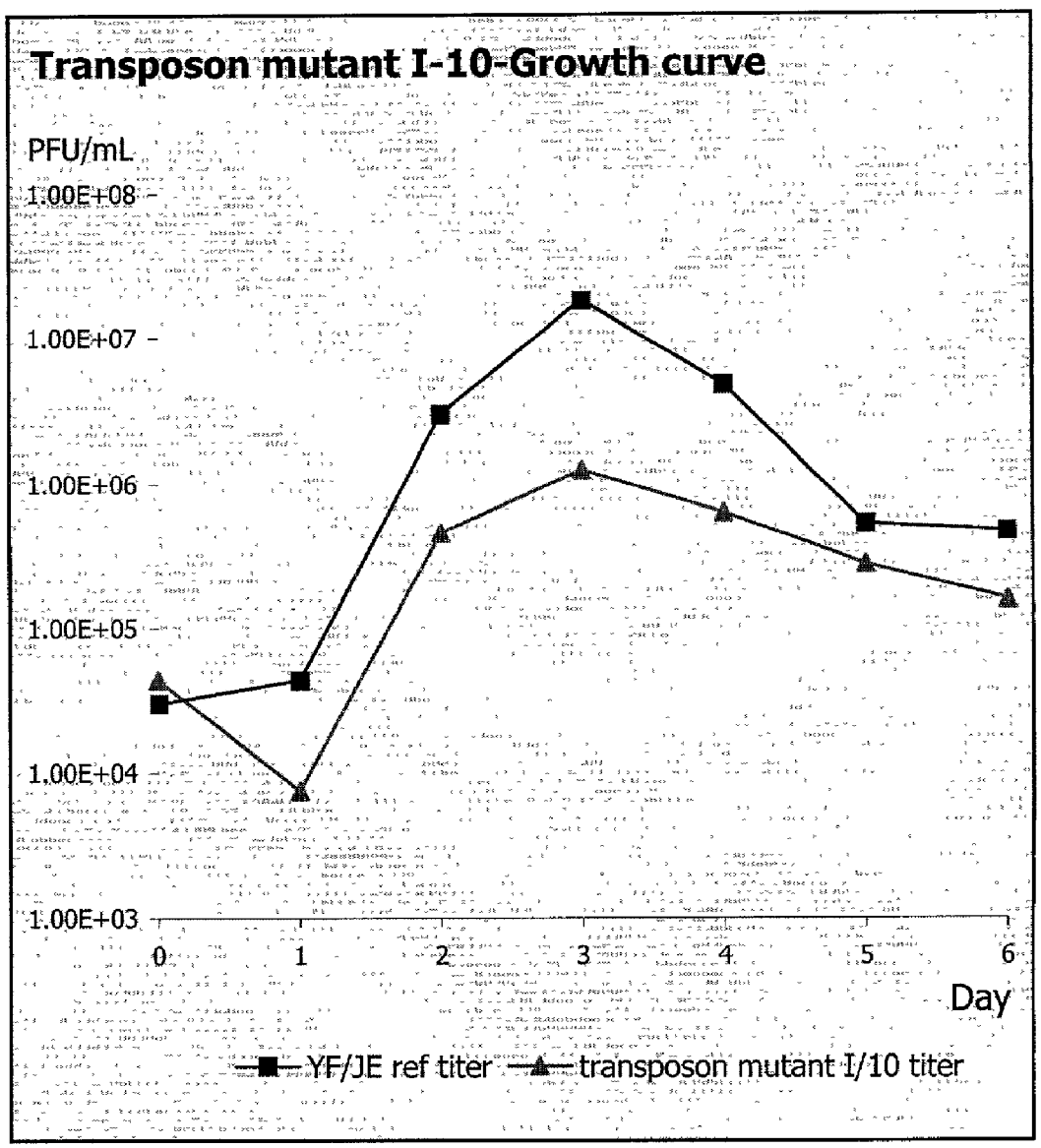
FIG. 10 is a graph showing the growth properties of the I-10 infectious clone. The line with the triangles corresponds to the titer of the transposon mutant I-10, while the line with the squares corresponds to the titer of the YF/JE parent virus.

The biological properties of transposon mutant I-10 were determined and compared with those of CHIMERIVAX™-JE (chimeric flavivirus comprising capsid and non-structural proteins from yellow fever virus and pre-membrane and envelope proteins from Japanese encephalitis virus). First, the growth properties of clone I-10 were determined. As is shown in FIG. 10, the mutant infectious clone I-10 shows similar growth kinetics as the CHIMERIVAX™-JE (chimeric flavivirus comprising capsid and non-structural proteins from yellow fever virus and pre-membrane and envelope proteins from Japanese encephalitis virus) parent, but grows to a slightly lower titer, reaching 8e5 PFU/ml, as compared to 1e7 PFU/ml for YF/JE. Also, the mutant infectious clone I-10 was found to induce a cytopathic effect in Vero cells, analogous to its YF/JE parent.

Figure 11:
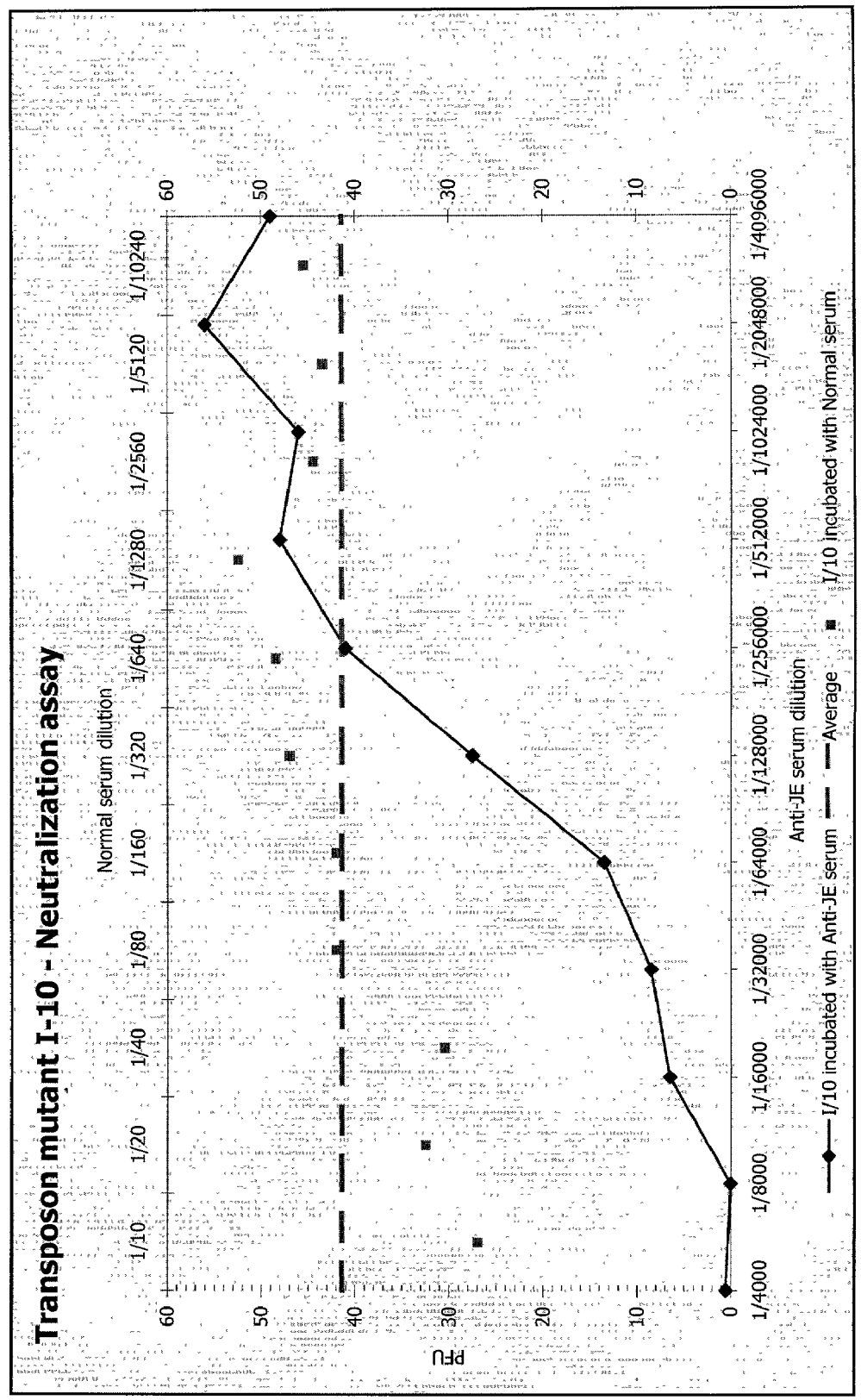
FIG. 11 is a graph showing the results of a neutralization assay of transposon mutant I-10. The line with the diamond corresponds to the titer of samples incubated with anti-JE serum, the squares correspond to samples incubated with normal serum, and the dashed line shows the average.
Figure 12:
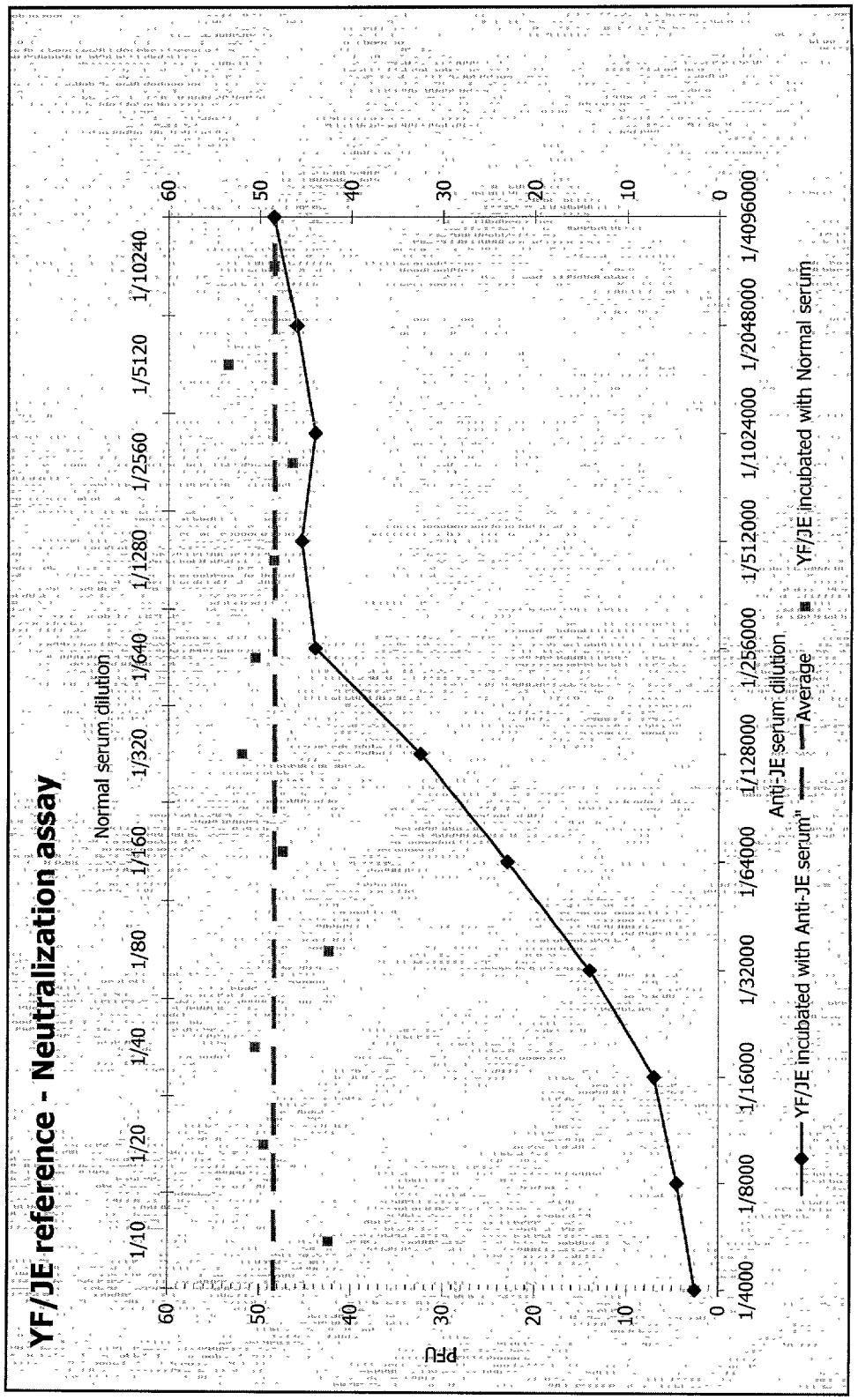
FIG. 12 is a graph showing the results of a neutralization assay of the YF/JE reference. The line with the diamond corresponds to the titer of samples incubated with anti-JE serum, the squares correspond to samples incubated with normal serum, and the dashed line shows the average.

Plaque reduction neutralization (PRNT) assays were then carried out. A preparation of anti-JE polyclonal antisera was shown to neutralize clone I-10 and CHIMERIVAX™-JE (chimeric flavivirus comprising capsid and non-structural proteins from yellow fever virus and pre-membrane and envelope proteins from Japanese encephalitis virus) to the same degree (1:64,000), confirming the feasibility of inserting foreign DNA into the envelope of the JE chimera without unduly affecting the structural integrity of the viral envelope (FIGS. 11 and 12). These experiments show that amino acid position 287 of the JE envelope in CHIMERIVAX™-JE (chimeric flavivirus comprising capsid and non-structural proteins from yellow fever virus and pre-membrane and envelope proteins from Japanese encephalitis virus) is permissive for the insertion of foreign DNA. We also provide evidence that amino acid positions 59, 231, 340, and 436 are permissive for insertion of foreign sequences.

TABLE 1

PCR Primers

For cloning into pUC19:

(SEQ ID NO:8)
TN1.F 5'-GCCGGTACCCACGATATCTCATGAAACTG-3'

(SEQ ID NO:9)
TN2.R 5'-CTGCAGACCATCCCGAATTCTGGAAAATGG-3'

For mapping studies:

(SEQ ID NO:10)
Not I/KAN-3 FP-2 5'-ACCTACAACAAAGCTCTCATCAACC-3'

(SEQ ID NO:11)
Not I/KAN-3 RP-2 5'-TCCCGTTGAATATGGCTCATAAC-3'

(SEQ ID NO:12)
TMOS.F 5'-CTGTCTCTTGTACACATCTTGCGGCCGC-3'

TABLE 1-continued

PCR Primers

For cDNA synthesis using SUPERSCRIPT ™ II RNase H
Reverse Trascriptase (Life Technologies):

FNOR 5'-CCTGGGGAGAACACAAGGTTC-3' (SEQ ID NO:13)

YF 2.6-5'-AAGAGGCTTTCACTATTGATG-3' (SEQ ID NO:14)

TABLE 2

List of examples of pathogens from which antigens/peptides can be derived

VIRUSES:
Flaviviridae

Yellow Fever virus
Japanese Encephalitis virus
Dengue virus, types 1, 2, 3 & 4
West Nile Virus
Tick Borne Encephalitis virus
Hepatitis C virus (e.g., genotypes
1a, 1b, 2a, 2b, 2c, 3a, 4a, 4b, 4c, and 4d)
Papoviridae:

Papillomavirus
Retroviridae

Human Immunodeficiency virus, type I
Human Immunodeficiency virus, type II
Simian Immunodeficiency virus
Human T lymphotropic virus, types I & II
Hepnaviridae Hepatitis B virus
Picornaviridae Hepatitis A virus
Rhinovirus
Poliovirus
Herpesviridae:

Herpes simplex virus, type I
Herpes simplex virus, type II
Cytomegalovirus
Epstein Barr virus
Varicella-Zoster virus
Togaviridae Alphavirus
Rubella virus TABLE 2-continued List of examples of pathogens from which antigens/peptides can be derived Paramyxoviridae:

Respiratory syncytial virus
Parainfluenza virus
Measles virus
Mumps virus
Orthomyxoviridae Influenza virus
Filoviridae Marburg virus
Ebola virus
Rotoviridae:

Rotavirus
Coronaviridae

Coronavirus
Adenoviridae

Adenovirus
Rhabdoviridae

Rabiesvirus
BACTERIA:

Enterotoxigenic *E. coli*
Enteropathogenic *E. coli*
*Campylobacter jejuni*
*Helicobacter pylori*
*Salmonella typhi*
*Vibrio cholerae*
*Clostridium difficile*
*Clostridium tetani*
*Streptococccus pyogenes*
*Bordetella pertussis*
*Neisseria meningitides*
*Neisseria gonorrhoea*
*Legionella neumophilus*
Clamydial spp.
Haemophilus spp.
Shigella spp.
PARASITES:

Plasmodium spp.
Schistosoma spp.
Trypanosoma spp.
Toxoplasma spp.
Cryptosporidia spp.
Pneumocystis spp.
Leishmania spp.

TABLE 3

Examples of select antigens from listed viruses

| VIRUS | ANTIGEN |
|---|---|
| Flaviviridae | |
| Yellow Fever virus | Nucleocapsid, M & E glycoproteins |
| Japanese Encephalitis virus | Nucleocapsid, M & E glycoproteins |
| Dengue virus, types 1, 2, 3 & 4 | Nucleocapsid, M & E glycoproteins |
| West Nile Virus | Nucleocapsid, M & E glycoproteins |
| Tick Borne Encephalitis virus | Nucleocapsid, M & E glycoproteins |
| Hepatitis C virus | Nucleocapsid, E1 & E2 glycoproteins |

TABLE 3-continued

Examples of select antigens from listed viruses

| VIRUS | ANTIGEN |
|---|---|
| Papoviridae: | |
| Papillomavirus | L1 & L2 capsid protein, E6 & E7 transforming protein (oncopgenes) |
| Retroviridae | |
| Human Immunodeficiency virus, type I | gag, pol, vif, tat, vpu, env, nef |
| Human Immunodeficiency virus, type II | gag, pol, vif, tat, vpu, env, nef |
| Simian Immunodeficiency virus | gag, pol, vif, tat, vpu, env, nef |
| Human T lymphotropic virus, types I & II | gag, pol, env |

TABLE 4

Examples of B and T cell epitopes from listed viruses/antigens

| VIRUS | ANTIGEN | EPITOPE | LOCATION | SEQUENCE (5'-3') |
|---|---|---|---|---|
| *Flaviviridae* | | | | |
| Hepatitis C | Nucleocapsid | CTL | 2-9 | STNPKPQR (SEQ ID NO:15) |
| | | | 35-44 | YLLPRRGPRL (SEQ ID NO:16) |
| | | | 41-49 | GPRLGVRAT (SEQ ID NO:17) |
| | | | 81-100 | YPWPLYGNEGCGWAGWLLSP (SEQ ID NO:18) |
| | | | 129-144 | GFADLMGYIPLVGAPL (SEQ ID NO:19) |
| | | | 132-140 | DLMGYIPLV (SEQ ID NO:20) |
| | | | 178-187 | LLALLSCLTV (SEQ ID NO:21) |
| | E1 glycoprotein | CTL | 231-250 | REGNASRCWVAVTPTVATRD (SEQ ID NO:22) |
| | E2 glycoprotein | CTL | 686-694 | STGLIHLHQ (SEQ ID NO:23) |
| | | | 725-734 | LLADARVCSC (SEQ ID NO:24) |
| | | | 489-496 | CWHYPPRPCGI (SEQ ID NO:25) |
| | | | 569-578 | CVIGGVGNNT (SEQ ID NO:26) |
| | | | 460-469 | RRLTDFAQGW (SEQ ID NO:27) |
| | | | 621-628 | TINYTIFK (SEQ ID NO:28) |
| | B cell | | 384-410 | ETHVTGGNAGRTTAGLVGLLTPGAKQN (SEQ ID NO:29) |
| | | | 411-437 | IQLINTNGSWHINSTALNCNESLNTGW (SEQ ID NO:30) |
| | | | 441-460 | LFYQHKFNSSGCPERLASCR (SEQ ID NO:31) |
| | | | 511-546 | PSPVVVGTTDRSGAPTYSWGANDTDVFVLNNTRPPL (SEQ ID NO:32) |
| | T helper | | 411-416 | IQLINT (SEQ ID NO:33) |
| *Papoviridae* | | | | |
| HPV 16 | E7 | T helper | 48-54 | DRAHYNI (SEQ ID NO:34) |
| | | CTL | 49-57 | RAHYNIVTF (SEQ ID NO:35) |
| | | B cell | 10-14 | EYMLD (SEQ ID NO:36) |
| | | | 38-41 | IDGP (SEQ ID NO:37) |
| | | | 44-48 | QAEPD (SEQ ID NO:38) |
| HPV 18 | E7 | T helper | 44-55 | VNHQHLPARRA (SEQ ID NO:39) |
| | | | 81-90 | DDLRAFQQLF (SEQ ID NO:40) |

---

What is claimed is:

1. A flavivirus vector comprising capsid and non-structural proteins of a yellow fever virus vaccine strain, a flavivirus membrane protein, and a flavivirus envelope protein into which a foreign peptide is inserted, wherein said foreign peptide in said flavivirus vector is immunogenic.

2. The flavivirus vector of claim 1, wherein said vector is a chimeric flavivirus in which the membrane and envelope proteins are of a flavivirus other than a yellow fever virus.

3. The flavivirus vector of claim 2, wherein said flavivirus other than a yellow fever virus is a Japanese encephalitis virus.

4. The flavivirus vector of claim 2, wherein said flavivirus other than a yellow fever virus is selected from the group consisting of Japanese encephalitis, Dengue-1, Dengue-2, Dengue-3, Dengue-4, Murray Valley encephalitis, St. Louis encephalitis, West Nile, Kunjin, Rocio encephalitis, Ilheus, ticke-borne encephalitis, Central European encephalitis, Siberian encephalitis, Russian Spring-Summer encephalitis, Kyasanur Forest Disease, Omsk Hemorrhagic fever, Louping ill, Powassan, Negishi, Absettarov, Hansalova, Apoi, and Hypr viruses.

5. The flavivirus vector of claim 1, wherein said yellow fever virus vaccine strain is YF 17D.

6. The flavivirus vector of claim 1, wherein said foreign peptide comprises an epitope from an antigen of a viral, bacterial, or parasitic pathogen.

7. The flavivirus vector of claim 6, wherein said pathogen is selected from the group consisting of hepatitis C virus, human papillomavirus, human immunodeficiency virus, hepatitis B virus, herpes simplex virus, influenza virus, and *Clostridium difficile*.

8. The flavivirus vector of claim 7, wherein said pathogen is an influenza virus.

9. The flavivirus vector of claim 1, wherein said foreign peptide comprises an epitope from a tumor-associated antigen.

10. A pharmaceutical composition comprising the flavivirus vector of claim 1 and a pharmaceutically acceptable carrier or diluent.

11. The pharmaceutical composition of claim 10, wherein said flavivirus vector is a chimeric flavivirus in which the membrane and envelope proteins are of a flavivirus other than a yellow fever virus.

12. The pharmaceutical composition of claim 11, wherein said flavivirus vector is a chimeric flavivirus in which the membrane and envelope proteins are of a Japanese encephalitis virus.

13. The pharmaceutical composition of claim 11, wherein flavivirus other than a yellow fever virus is selected from the group consisting of Japanese encephalitis, Dengue- 1, Dengue-2, Dengue-3, Dengue-4, Murray Valley encephalitis, St. Louis encephalitis, West Nile, Kunjin, Rocio encephalitis, Ilheus, ticke-borne encephalitis, Central European encephalitis, Siberian encephalitis, Russian Spring-Summer encephalitis, Kyasanur Forest Disease, Omsk Hemorrhagic fever, Louping ill, Powassan, Negishi, Absettarov, Hansalova, Apoi, and Hypr viruses.

14. The pharmaceutical composition of claim 10, said yellow fever virus vaccine strain is YF 17D.

15. The pharmaceutical composition of claim 10, wherein said foreign peptide comprises an epitope from an antigen of a viral, bacterial, or parasitic pathogen.

16. The pharmaceutical composition of claim 15, wherein said pathogen is selected from the group consisting of hepatitis C virus, human papillomavirus, human immunodeficiency virus, hepatitis B virus, herpes simplex virus, influenza virus, and *Clostridium difficile*.

17. The pharmaceutical composition of claim 16, wherein said pathogen is an influenza virus.

18. The pharmaceutical composition of claim 10, wherein said foreign peptide comprises an epitope from a tumor-associated antigen.

19. A method of delivering a peptide to a patient, said method comprising administering to said patient the composition of claim 10.

20. The method of claim 19, wherein the peptide is an antigen and said administration is carried out to induce an immune response to a pathogen or tumor from which said antigen is derived.

21. The flavivirus vector of claim 1, wherein the membrane and envelope proteins are of a yellow fever virus vaccine strain.

22. The flavivirus of claim 21, wherein the yellow fever virus vaccine strain is YF 17D.

23. A method for identifying a site in the envelope protein of a chimeric flavivirus or a genetically attenuated flavivirus that is permissive for insertion of a foreign peptide, said method comprising the steps of:

(i) introducing a nucleic acid molecule encoding a foreign peptide into a gene encoding a flavivirus envelope protein;
(ii) generating a flavivirus vector comprising an envelope protein encoded by said gene, wherein said envelope protein comprises said foreign peptide; and
(iii) determining whether the flavivirus vector generated in step (ii) is permissive for said insertion.

24. The method of claim 23, wherein said flavivirus vector is a chimeric flavivirus vector comprising the capsid and non-structural proteins of a first flavivirus and the pre-membrane and envelope proteins of a second flavivirus.

25. The method of claim 24, wherein said first flavivirus is selected from the group consisting of Japanese encephalitis, Dengue-1, Dengue-2, Dengue-3, Dengue-4, Yellow fever, Murray Valley encephalitis, St. Louis encephalitis, West Nile, Kunjin, Rocio encephalitis, Ilheus, ticke-borne encephalitis, Central European encephalitis, Siberian encephalitis, Russian Spring-Summer encephalitis, Kyasanur Forest Disease, Omsk Hemorrhagic fever, Louping ill, Powassan, Negishi, Absettarov, Hansalova, Apoi, and Hypr viruses.

26. The method of claim 25, wherein said first flavivirus is a Yellow Fever virus.

27. The method of claim 24, wherein said second flavivirus is selected from the group consisting of Japanese encephalitis, Dengue-1, Dengue-2, Dengue-3, Dengue-4, Yellow fever, Murray Valley encephalitis, St. Louis encephalitis, West Nile, Kunjin, Rocio encephalitis, Ilheus, ticke-borne encephalitis, Central European encephalitis, Siberian encephalitis, Russian Spring-Summer encephalitis, Kyasanur Forest Disease, Omsk Hemorrhagic fever, Louping ill, Powassan, Negishi, Absettarov, Hansalova, Apoi, and Hypr viruses.

28. The method of claim 27, wherein said second flavivirus is a Japanese Encephalitis.

29. The method of claim 23, wherein said foreign peptide comprises an epitope derived from an antigen of a viral, bacterial, or parasitic pathogen.

30. The method of claim 29, wherein said pathogen is selected from the group consisting of hepatitis C virus, human papillomavirus, human immunodeficiency virus, hepatitis B virus, herpes simplex virus, influenza virus, and *Clostridium difficile*.

31. The method of claim 30, wherein said pathogen is an influenza virus.

32. The method of claim 23, wherein said foreign peptide comprises an epitope derived from a tumor-associated antigen.

33. The method of claim 23, wherein said nucleic acid molecule is introduced into said envelope gene randomly by transposon mutagenesis.

34. The method of claim 23, wherein determination of whether said flavivirus vector generated in step (ii) is permissive for said insertion is carried out by analysis of (a) the infectivity of said flavivirus vector, (b) the stability of the sequence of the foreign protein upon multiple passages of the vector, (c) the growth properties of said flavivirus vector, or (d) whether the flavivirus vector can be neutralized with antibodies against the envelope protein of said first flavivirus.

35. The method of claim 34, further comprising comparing the analysis of the flavivirus vector with a similar analysis of the flavivirus from which it was derived.

36. The method of claim 23, wherein said genetically attenuated flavivirus is Yellow Fever YF 17D.

37. A nucleic acid molecule comprising the genome of the flavivirus of claim 23 or the complement thereof.

* * * * *

UNITED STATES PATENT AND TRADEMARK OFFICE
CERTIFICATE OF CORRECTION

| | |
|---|---|
| PATENT NO. | : 7,569,383 B2 |
| APPLICATION NO. | : 10/160939 |
| DATED | : August 4, 2009 |
| INVENTOR(S) | : Kleanthous et al. |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 597 days.

Signed and Sealed this

Seventh Day of September, 2010

David J. Kappos
*Director of the United States Patent and Trademark Office*

SEQUENCE LISTING

```
<160> NUMBER OF SEQ ID NOS: 40

<210> SEQ ID NO 1
<211> LENGTH: 33
<212> TYPE: PRT
<213> ORGANISM: Artificial Sequence
<220> FEATURE:
<223> OTHER INFORMATION: synthetic

<400> SEQUENCE: 1

Thr Ser Pro Ser Ser Thr Cys Leu Leu Tyr Thr Ser Cys Gly Arg Leu
1               5                   10                  15

Met Cys Thr Arg Asp Ser Ser Ser Thr Ala Trp Arg Asn Arg Glu Leu
            20                  25                  30
```

Leu

<210> SEQ ID NO 2
<211> LENGTH: 33
<212> TYPE: PRT
<213> ORGANISM: Artificial Sequence
<220> FEATURE:
<223> OTHER INFORMATION: synthetic

<400> SEQUENCE: 2

```
Val Val Glu Tyr Ser Ser Val Ser Cys Thr His Leu Ala Ala Ala
1               5                   10                  15

Arg Cys Val Gln Glu Thr Tyr Ser Ser Ser Val Met Leu Thr Ser Gly
                20                  25                  30

His
```

<210> SEQ ID NO 3
<211> LENGTH: 33
<212> TYPE: PRT
<213> ORGANISM: Artificial Sequence
<220> FEATURE:
<223> OTHER INFORMATION: synthetic

<400> SEQUENCE: 3

```
Ala Glu Val Arg Ser Tyr Cys Leu Leu Tyr Thr Ser Cys Gly Arg Leu
1               5                   10                  15

Met Cys Thr Arg Asp Ser Arg Ser Tyr Cys Tyr His Ala Ser Val Thr
                20                  25                  30

Asp
```

<210> SEQ ID NO 4
<211> LENGTH: 33
<212> TYPE: PRT
<213> ORGANISM: Artificial Sequence
<220> FEATURE:
<223> OTHER INFORMATION: synthetic

<400> SEQUENCE: 4

```
Gly Gly Val Phe Asn Ser Cys Leu Leu Tyr Thr Ser Cys Gly Arg Leu
1               5                   10                  15

Met Cys Thr Arg Asp Ser Phe Asn Ser Ile Gly Arg Ala Val His Gln
                20                  25                  30

Val
```

<210> SEQ ID NO 5
<211> LENGTH: 33
<212> TYPE: PRT
<213> ORGANISM: Artificial Sequence
<220> FEATURE:
<223> OTHER INFORMATION: synthetic

<400> SEQUENCE: 5

```
Thr Glu Lys Phe Ser Phe Cys Leu Leu Tyr Thr Ser Cys Gly Arg Leu
1               5                   10                  15

Met Cys Thr Arg Asp Ser Phe Ser Phe Ala Lys Asn Pro Val Asp Thr
                20                  25                  30

Gly
```

<210> SEQ ID NO 6
<211> LENGTH: 77
<212> TYPE: DNA
<213> ORGANISM: Artificial Sequence

```
<220> FEATURE:
<223> OTHER INFORMATION: synthetic

<400> SEQUENCE: 6
ggagtactca agctctgtct cttgtacaca tcttgcggcc gcaagatgtg tacaagagac    60
agactcaagc tcagtga                                                  77

<210> SEQ ID NO 7
<211> LENGTH: 25
<212> TYPE: PRT
<213> ORGANISM: Artificial Sequence
<220> FEATURE:
<223> OTHER INFORMATION: synthetic

<400> SEQUENCE: 7

Glu Tyr Ser Ser Ser Val Ser Cys Thr His Leu Ala Ala Ala Arg Cys
1               5                   10                  15

Val Gln Glu Thr Asp Ser Ser Ser Val
            20                  25

<210> SEQ ID NO 8
<211> LENGTH: 29
<212> TYPE: DNA
<213> ORGANISM: Artificial Sequence
<220> FEATURE:
<223> OTHER INFORMATION: synthetic

<400> SEQUENCE: 8
gccggtaccc acgatatctc atgaaactg                                     29

<210> SEQ ID NO 9
<211> LENGTH: 30
<212> TYPE: DNA
<213> ORGANISM: Artificial Sequence
<220> FEATURE:
<223> OTHER INFORMATION: synthetic

<400> SEQUENCE: 9
ctgcagacca tcccgaattc tggaaaatgg                                    30

<210> SEQ ID NO 10
<211> LENGTH: 25
<212> TYPE: DNA
<213> ORGANISM: Artificial Sequence
<220> FEATURE:
<223> OTHER INFORMATION: synthetic

<400> SEQUENCE: 10
acctacaaca aagctctcat caacc                                         25

<210> SEQ ID NO 11
<211> LENGTH: 23
<212> TYPE: DNA
<213> ORGANISM: Artificial Sequence
<220> FEATURE:
<223> OTHER INFORMATION: synthetic

<400> SEQUENCE: 11
tcccgttgaa tatggctcat aac                                           23

<210> SEQ ID NO 12
<211> LENGTH: 28
<212> TYPE: DNA
<213> ORGANISM: Artificial Sequence
<220> FEATURE:
```

-continued

<223> OTHER INFORMATION: synthetic

<400> SEQUENCE: 12
ctgtctcttg tacacatctt gcggccgc                              28

<210> SEQ ID NO 13
<211> LENGTH: 21
<212> TYPE: DNA
<213> ORGANISM: Artificial Sequence
<220> FEATURE:
<223> OTHER INFORMATION: synthetic

<400> SEQUENCE: 13
cctggggaga acacaaggtt c                                     21

<210> SEQ ID NO 14
<211> LENGTH: 21
<212> TYPE: DNA
<213> ORGANISM: Artificial Sequence
<220> FEATURE:
<223> OTHER INFORMATION: synthetic

<400> SEQUENCE: 14
aagaggcttt cactattgat g                                     21

<210> SEQ ID NO 15
<211> LENGTH: 8
<212> TYPE: PRT
<213> ORGANISM: Hepatitis C Virus

<400> SEQUENCE: 15

Ser Thr Asn Pro Lys Pro Gln Arg
1               5

<210> SEQ ID NO 16
<211> LENGTH: 10
<212> TYPE: PRT
<213> ORGANISM: Hepatitis C Virus

<400> SEQUENCE: 16

Tyr Leu Leu Pro Arg Arg Gly Pro Arg Leu
1               5                   10

<210> SEQ ID NO 17
<211> LENGTH: 9
<212> TYPE: PRT
<213> ORGANISM: Hepatitis C Virus

<400> SEQUENCE: 17

Gly Pro Arg Leu Gly Val Arg Ala Thr
1               5

<210> SEQ ID NO 18
<211> LENGTH: 20
<212> TYPE: PRT
<213> ORGANISM: Hepatitis C Virus

<400> SEQUENCE: 18

Tyr Pro Trp Pro Leu Tyr Gly Asn Glu Gly Cys Gly Trp Ala Gly Trp
1               5                   10                  15

Leu Leu Ser Pro
            20

<210> SEQ ID NO 19

```
<211> LENGTH: 16
<212> TYPE: PRT
<213> ORGANISM: Hepatitis C Virus

<400> SEQUENCE: 19

Gly Phe Ala Asp Leu Met Gly Tyr Ile Pro Leu Val Gly Ala Pro Leu
1               5                   10                  15

<210> SEQ ID NO 20
<211> LENGTH: 9
<212> TYPE: PRT
<213> ORGANISM: Hepatitis C Virus

<400> SEQUENCE: 20

Asp Leu Met Gly Tyr Ile Pro Leu Val
1               5

<210> SEQ ID NO 21
<211> LENGTH: 10
<212> TYPE: PRT
<213> ORGANISM: Hepatitis C Virus

<400> SEQUENCE: 21

Leu Leu Ala Leu Leu Ser Cys Leu Thr Val
1               5                   10

<210> SEQ ID NO 22
<211> LENGTH: 20
<212> TYPE: PRT
<213> ORGANISM: Hepatitis C Virus

<400> SEQUENCE: 22

Arg Glu Gly Asn Ala Ser Arg Cys Trp Val Ala Val Thr Pro Thr Val
1               5                   10                  15

Ala Thr Arg Asp
            20

<210> SEQ ID NO 23
<211> LENGTH: 9
<212> TYPE: PRT
<213> ORGANISM: Hepatitis C Virus

<400> SEQUENCE: 23

Ser Thr Gly Leu Ile His Leu His Gln
1               5

<210> SEQ ID NO 24
<211> LENGTH: 10
<212> TYPE: PRT
<213> ORGANISM: Hepatitis C Virus

<400> SEQUENCE: 24

Leu Leu Ala Asp Ala Arg Val Cys Ser Cys
1               5                   10

<210> SEQ ID NO 25
<211> LENGTH: 11
<212> TYPE: PRT
<213> ORGANISM: Hepatitis C Virus

<400> SEQUENCE: 25

Cys Trp His Tyr Pro Pro Arg Pro Cys Gly Ile
1               5                   10
```

<210> SEQ ID NO 26
<211> LENGTH: 10
<212> TYPE: PRT
<213> ORGANISM: Hepatitis C Virus

<400> SEQUENCE: 26

Cys Val Ile Gly Gly Val Gly Asn Asn Thr
1               5                   10

<210> SEQ ID NO 27
<211> LENGTH: 10
<212> TYPE: PRT
<213> ORGANISM: Hepatitis C Virus

<400> SEQUENCE: 27

Arg Arg Leu Thr Asp Phe Ala Gln Gly Trp
1               5                   10

<210> SEQ ID NO 28
<211> LENGTH: 8
<212> TYPE: PRT
<213> ORGANISM: Hepatitis C Virus

<400> SEQUENCE: 28

Thr Ile Asn Tyr Thr Ile Phe Lys
1               5

<210> SEQ ID NO 29
<211> LENGTH: 27
<212> TYPE: PRT
<213> ORGANISM: Hepatitis C Virus

<400> SEQUENCE: 29

Glu Thr His Val Thr Gly Gly Asn Ala Gly Arg Thr Thr Ala Gly Leu
1               5                   10                  15

Val Gly Leu Leu Thr Pro Gly Ala Lys Gln Asn
            20                  25

<210> SEQ ID NO 30
<211> LENGTH: 27
<212> TYPE: PRT
<213> ORGANISM: Hepatitis C Virus

<400> SEQUENCE: 30

Ile Gln Leu Ile Asn Thr Asn Gly Ser Trp His Ile Asn Ser Thr Ala
1               5                   10                  15

Leu Asn Cys Asn Glu Ser Leu Asn Thr Gly Trp
            20                  25

<210> SEQ ID NO 31
<211> LENGTH: 20
<212> TYPE: PRT
<213> ORGANISM: Hepatitis C Virus

<400> SEQUENCE: 31

Leu Phe Tyr Gln His Lys Phe Asn Ser Ser Gly Cys Pro Glu Arg Leu
1               5                   10                  15

Ala Ser Cys Arg
            20

<210> SEQ ID NO 32
<211> LENGTH: 36
<212> TYPE: PRT
<213> ORGANISM: Hepatitis C Virus

```
<400> SEQUENCE: 32

Pro Ser Pro Val Val Val Gly Thr Thr Asp Arg Ser Gly Ala Pro Thr
1               5                   10                  15

Tyr Ser Trp Gly Ala Asn Asp Thr Asp Val Phe Val Leu Asn Asn Thr
            20                  25                  30

Arg Pro Pro Leu
        35

<210> SEQ ID NO 33
<211> LENGTH: 6
<212> TYPE: PRT
<213> ORGANISM: Hepatitis C Virus

<400> SEQUENCE: 33

Ile Gln Leu Ile Asn Thr
1               5

<210> SEQ ID NO 34
<211> LENGTH: 7
<212> TYPE: PRT
<213> ORGANISM: Human Papilloma Virus, strain 16

<400> SEQUENCE: 34

Asp Arg Ala His Tyr Asn Ile
1               5

<210> SEQ ID NO 35
<211> LENGTH: 9
<212> TYPE: PRT
<213> ORGANISM: Human Papilloma Virus, strain 16

<400> SEQUENCE: 35

Arg Ala His Tyr Asn Ile Val Thr Phe
1               5

<210> SEQ ID NO 36
<211> LENGTH: 5
<212> TYPE: PRT
<213> ORGANISM: Human Papilloma Virus, strain 16

<400> SEQUENCE: 36

Glu Tyr Met Leu Asp
1               5

<210> SEQ ID NO 37
<211> LENGTH: 4
<212> TYPE: PRT
<213> ORGANISM: Human Papilloma Virus, strain 16

<400> SEQUENCE: 37

Ile Asp Gly Pro
1

<210> SEQ ID NO 38
<211> LENGTH: 5
<212> TYPE: PRT
<213> ORGANISM: Human Papilloma Virus, strain 16

<400> SEQUENCE: 38

Gln Ala Glu Pro Asp
1               5
```

```
-continued

<210> SEQ ID NO 39
<211> LENGTH: 11
<212> TYPE: PRT
<213> ORGANISM: Human Papilloma Virus, strain 18

<400> SEQUENCE: 39

Val Asn His Gln His Leu Pro Ala Arg Arg Ala
1               5                   10

<210> SEQ ID NO 40
<211> LENGTH: 10
<212> TYPE: PRT
<213> ORGANISM: Human Papilloma Virus, strain 18

<400> SEQUENCE: 40

Asp Asp Leu Arg Ala Phe Gln Gln Leu Phe
1               5                   10
```